US011774420B2

(12) United States Patent
Black et al.

(10) Patent No.: US 11,774,420 B2
(45) Date of Patent: Oct. 3, 2023

(54) METHOD AND APPARATUS FOR QUANTITATIVELY ANALYZING A GASEOUS PROCESS STREAM

(71) Applicant: SHELL USA, INC., Houston, TX (US)

(72) Inventors: Jesse Raymond Black, Houston, TX (US); Julie Michelle Freelin, Houston, TX (US); Richard Kenneth Oldfield, Amsterdam (NL); Gregory John Ward, Houston, TX (US)

(73) Assignee: SHELL USA, INC., Houston, TX (US)

( * ) Notice: Subject to any disclaimer, the term of this patent is extended or adjusted under 35 U.S.C. 154(b) by 0 days.

(21) Appl. No.: 17/852,005

(22) Filed: Jun. 28, 2022

(65) Prior Publication Data

US 2022/0334095 A1 Oct. 20, 2022

Related U.S. Application Data

(62) Division of application No. 16/341,216, filed as application No. PCT/EP2017/076069 on Oct. 12, 2017, now Pat. No. 11,408,869.

(30) Foreign Application Priority Data

Oct. 14, 2016 (EP) .................................... 16193878

(51) Int. Cl.
G01N 33/00 (2006.01)
B01J 4/00 (2006.01)
(Continued)

(52) U.S. Cl.
CPC .......... *G01N 33/0006* (2013.01); *B01J 4/008* (2013.01); *B01J 8/0457* (2013.01);
(Continued)

(58) Field of Classification Search
CPC ..... G01N 2030/025; G01N 2030/8845; G01N 2030/8886; G01N 30/06; G01N 30/24;
(Continued)

(56) References Cited

U.S. PATENT DOCUMENTS 2,289,063 A 1/1942 Ocon et al.
3,573,201 A 3/1971 Annesser et al.
(Continued)

FOREIGN PATENT DOCUMENTS

CN 102580590 A 7/2012
CN 103528878 A 1/2014
(Continued)

OTHER PUBLICATIONS

International Search Report and Written Opinion received for PCT Patent Application No. PCT/EP2017/076069, dated Nov. 23, 2017, 8 pages.
(Continued)

*Primary Examiner* — Harshad R Patel
*Assistant Examiner* — Gedeon M Kidanu
(74) *Attorney, Agent, or Firm* — SHELL USA, INC.

(57) ABSTRACT

The present invention relates to method and an apparatus for quantitatively analyzing a gaseous process stream, in particular a stream from a process for producing ethylene carbonate and/or ethylene glycol, in particular where such stream comprises gaseous organic iodides.

2 Claims, 8 Drawing Sheets

(51) Int. Cl.
| | |
|---|---|
| *B01J 8/04* | (2006.01) |
| *G01N 30/06* | (2006.01) |
| *G01N 30/24* | (2006.01) |
| *G01N 30/68* | (2006.01) |
| *G01N 30/70* | (2006.01) |
| *G01N 30/88* | (2006.01) |
| *C07C 31/20* | (2006.01) |
| *C07D 317/38* | (2006.01) |
| *G01N 30/02* | (2006.01) |

(52) U.S. Cl.
CPC ............ *G01N 30/06* (2013.01); *G01N 30/24* (2013.01); *G01N 30/68* (2013.01); *G01N 30/70* (2013.01); *G01N 30/88* (2013.01); *B01J 2208/00964* (2013.01); *B01J 2219/00247* (2013.01); *C07C 31/202* (2013.01); *C07D 317/38* (2013.01); *G01N 2030/025* (2013.01); *G01N 2030/8845* (2013.01); *G01N 2030/8886* (2013.01)

(58) Field of Classification Search
CPC ........ G01N 30/68; G01N 30/70; G01N 30/88; G01N 33/0006
See application file for complete search history.

(56) References Cited

U.S. PATENT DOCUMENTS

| | | | |
|---|---|---|---|
| 4,048,096 A | 9/1977 | Bissot | |
| 4,275,752 A * | 6/1981 | Collier | G05D 7/0106 137/7 |
| 4,761,394 A | 8/1988 | Lauritzen | |
| 4,766,105 A | 8/1988 | Lauritzen | |
| 4,789,528 A | 12/1988 | Owen et al. | |
| 5,157,957 A | 10/1992 | Mettes et al. | |
| 5,179,057 A | 1/1993 | Bissot | |
| 5,189,004 A | 2/1993 | Bartley | |
| 5,214,952 A | 6/1993 | Leggett et al. | |
| 5,239,856 A * | 8/1993 | Mettes | G01N 33/0018 73/1.05 |
| 5,380,697 A | 1/1995 | Matusz et al. | |
| 5,587,519 A * | 12/1996 | Ronge | G01N 33/0006 73/31.03 |
| 5,635,620 A * | 6/1997 | Ronge | G01N 33/0006 73/1.05 |
| 5,739,075 A | 4/1998 | Matusz | |
| 5,763,691 A | 6/1998 | Kawabe et al. | |
| 5,849,937 A | 12/1998 | Jubin, Jr. et al. | |
| 5,937,886 A * | 8/1999 | Girard | G01N 33/0006 137/599.08 |
| 6,040,467 A | 3/2000 | Papavassiliou et al. | |
| 6,217,659 B1 * | 4/2001 | Botelho | B01F 23/19 118/726 |
| 6,286,451 B1 * | 9/2001 | Ishikawa | C23C 16/4405 118/724 |
| 6,368,998 B1 | 4/2002 | Lockemeyer | |
| 6,603,038 B1 | 8/2003 | Hagemeyer et al. | |
| 6,656,874 B2 | 12/2003 | Lockemeyer | |
| 7,030,056 B2 | 4/2006 | Birke et al. | |
| 7,193,094 B2 | 3/2007 | Chipman et al. | |
| 7,425,647 B2 | 9/2008 | Lemanski et al. | |
| 8,063,256 B2 | 11/2011 | Van Kruchten | |
| 8,154,034 B1 | 4/2012 | Zhang et al. | |
| 8,318,004 B2 | 11/2012 | Drnevich et al. | |
| 8,546,592 B2 | 10/2013 | Evans et al. | |
| 8,569,527 B2 | 10/2013 | Matusz | |
| 8,591,634 B2 | 11/2013 | Winchester et al. | |
| 8,845,975 B2 | 9/2014 | Henstock et al. | |
| 8,858,893 B2 | 10/2014 | Evans et al. | |
| 8,894,838 B2 | 11/2014 | Dindi et al. | |
| 8,921,586 B2 | 12/2014 | Matusz | |
| 8,932,979 B2 | 1/2015 | Matusz et al. | |
| 9,116,526 B2 | 8/2015 | Hashimoto et al. | |
| 9,365,535 B2 | 6/2016 | Van Kruchten et al. | |
| 9,527,787 B2 | 12/2016 | Evans et al. | |
| 9,731,261 B2 | 8/2017 | Holdsworth et al. | |
| 10,279,280 B2 | 5/2019 | Wilkinson et al. | |
| 10,450,287 B2 | 10/2019 | Evans et al. | |
| 10,525,409 B2 | 1/2020 | Lemanski et al. | |
| 10,526,300 B2 | 1/2020 | Evans et al. | |
| 11,000,819 B2 | 5/2021 | Black et al. | |
| 2003/0204101 A1 | 10/2003 | Jewson et al. | |
| 2005/0000981 A1 | 1/2005 | Peng et al. | |
| 2005/0120877 A1 * | 6/2005 | Wu | C01C 1/024 95/117 |
| 2006/0070918 A1 | 4/2006 | Seapan et al. | |
| 2007/0173655 A1 | 7/2007 | Grey | |
| 2008/0281118 A1 | 11/2008 | Matusz | |
| 2009/0050535 A1 | 2/2009 | Evans | |
| 2009/0270640 A1 | 10/2009 | Maurer et al. | |
| 2009/0292132 A1 | 11/2009 | Evans | |
| 2011/0034710 A1 | 2/2011 | Matusz | |
| 2012/0152364 A1 * | 6/2012 | Hashimoto | G05D 11/132 137/605 |
| 2014/0001089 A1 | 1/2014 | Bazer-Bachi et al. | |
| 2014/0157865 A1 * | 6/2014 | Kim | G01N 30/463 73/23.4 |
| 2016/0004643 A1 | 1/2016 | Gaschwind et al. | |
| 2016/0023963 A1 | 1/2016 | Maat et al. | |
| 2016/0204643 A1 | 7/2016 | Manova-Elssibony | |
| 2017/0129827 A1 | 5/2017 | Dittrich | |
| 2017/0291119 A1 | 10/2017 | Wilkinson et al. | |
| 2019/0317065 A1 | 10/2019 | Black et al. | |

FOREIGN PATENT DOCUMENTS

| | | |
|---|---|---|
| DE | 202012012866 U1 | 2/2014 |
| GB | 2107712 A | 5/1983 |
| JP | H0547843 U | 6/1993 |
| JP | 2003207496 A | 7/2003 |
| JP | 2003247984 A | 9/2003 |
| WO | 9908790 A1 | 2/1999 |

OTHER PUBLICATIONS

International Search Report and Written Opinion received for PCT Patent Application No. PCT/EP2016/080749, dated Feb. 17, 2017, 8 pages.
International Search Report and Written Opinion received for PCT Patent Application No. PCT/EP2016/080752, dated Apr. 4, 2017, 9 pages.
International Search Report and Written Opinion received for PCT Patent Application No. PCT/EP2016/080759, dated Apr. 4, 2017, 9 pages.
Evans et al., "Industrial Epoxidation Processes", Industrial Epoxidation Processes, Encyclopedia of Catalysis Wiley—Interscience), 2003, vol. 3, pp. 246-264.
Brunauer et al., "Adsorption of Gases in MultiMolecular Layers", Journal of American Chemical Society, Feb. 1938, vol. 60, Issue No. 2, pp. 309-319.
Kirk-Othmer, Encyclopedia of Chemical Technology, 4th Edition, vol. 9, pp. 915-959, 1994.
International Search Report and Written Opinion received for PCT Patent Application No. PCT/EP2016/080744, dated Mar. 14, 2017, 12 pages.
Davidson, "A Simple and Accurate Method for Calculating Viscosity of Gaseous Mixtures", Report of Investigations 9456, United States Department of the Interior, Bureau of Mines, 1993, pp. 1-17.
Dongsen, "Research Progress of Cocatalyst in Silver Catalyst for Ethylene Oxide", Petrochemical Technology, vol. 1, Issue No. 1, Dec. 31, 1997, pp. 58-62.

* cited by examiner

METHOD AND APPARATUS FOR QUANTITATIVELY ANALYZING A GASEOUS PROCESS STREAM

CROSS REFERENCE TO RELATED APPLICATIONS

This is a Divisional application of U.S. patent application Ser. No. 16/341,216, filed Apr. 11, 2019, which is a National stage (§ 371) application of International Application No PCT/EP2017/076069, filed Oct. 12, 2017, which claims priority of EP application No. 16193878.2, filed Oct. 14, 2016, which is incorporated herein by reference in its entirety.

FIELD OF THE INVENTION

The present invention relates to methods and associated systems for quantitatively analyzing a gaseous process stream, in particular a stream from a process for producing ethylene carbonate and/or ethylene glycol, in particular where such stream comprises organic iodides in the parts per billion and/or parts per trillion range.

BACKGROUND OF THE INVENTION

Ethylene glycol (EG) is a valuable industrial compound that is widely employed as starting material for the manufacture of polyester fibers and polyethylene terephthalate (PET) resins; it also finds application in automotive anti-freeze and hydraulic brake fluids, aircraft de-icers as well as in pharmaceutical products.

Ethylene glycol is normally prepared from ethylene oxide (EO). Ethylene oxide is in turn prepared by silver-catalyzed oxidation of ethylene. More specifically, ethylene and oxygen are passed over a silver oxide catalyst, typically at pressures of 10-30 bar and temperatures of 200-300° C., producing a product stream comprising ethylene oxide, carbon dioxide, ethylene, oxygen and water. In one well-known process, the ethylene oxide is then reacted with a large excess of water in a non-catalytic process, producing a glycol product stream comprising close to 90 wt % monoethylene glycol (MEG), the remainder being predominantly diethylene glycol (DEG), some triethylene glycol (TEG) and a small amount of higher homologues. In another well-known process, ethylene oxide is reacted with carbon dioxide in the presence of a catalyst to produce ethylene carbonate. The ethylene carbonate is subsequently hydrolyzed to provide ethylene glycol. Reaction via ethylene carbonate significantly improves the selectivity of ethylene oxide conversion to monoethylene glycol.

In the last few decades, many efforts have been directed towards the development of simplified processes and equipment for producing alkylene glycols from alkylenes, notably ethylene glycol from ethylene. For example, GB2107712 describes a process for preparing monoethylene glycol wherein the gases from the ethylene oxide (EO) reactor are supplied directly to a reactor wherein ethylene oxide is converted to ethylene carbonate or to a mixture of ethylene glycol and ethylene carbonate.

EP 0776890 describes a process wherein the gases from the ethylene epoxidation reactor are supplied to an absorber, wherein the absorbing solution mainly contains ethylene carbonate (EC) and ethylene glycol (EG). The ethylene oxide in the absorbing solution is supplied to a carboxylation reactor and allowed to react with carbon dioxide in the presence of a carboxylation catalyst. The ethylene carbonate in the absorbing solution is subsequently supplied, with the addition of water, to a separate hydrolysis reactor and subjected to hydrolysis in the presence of a hydrolysis catalyst.

EP2178815 describes a reactive absorption process for preparing monoethylene glycol, wherein the gases from the ethylene epoxidation reactor are supplied to a reactive absorber and the ethylene oxide is contacted with an aqueous lean absorbent in the presence of one or more carboxylation and hydrolysis catalysts, and wherein the majority of the ethylene oxide is converted to ethylene carbonate (EC) or ethylene glycol (EG) in the absorber.

In each of these cases, a gas stream containing gases that are not absorbed by the recirculating absorbent stream will be produced from the EO absorber or reactive absorber. This gas stream is treated in a carbon dioxide absorption column and then recombined with any gases bypassing the carbon dioxide absorption column. The combined gases are then at least partially recycled to the EO reactor.

The silver-based catalysts commonly employed in the conversion (epoxidation) of ethylene to ethylene oxide are very susceptible to catalyst poisoning, in particular poisoning by gaseous iodide-containing impurities, such as gaseous organic iodides. These gaseous organic iodides may originate from (partial) decomposition of the iodide-containing carboxylation catalysts and/or from exchange reactions with the one or more organic chloride-containing moderator (or "modifier") compounds that are typically added to the EO reactor for ethylene oxide catalyst performance control. Catalyst poisoning impacts the epoxidation catalyst performance, in particular the selectivity and/or the activity, and shortens the length of time the epoxidation catalyst can remain in the epoxidation reactor before it becomes necessary to exchange the catalyst with fresh catalyst.

Accordingly, it is desirable to remove such catalyst poisons as much as is practicable from the recycle gas stream before it comes into contact with the epoxidation catalyst. To this end, the application of one or more so-called "guard bed" systems positioned upstream of the EO reactor, as previously disclosed in, among others, EP2285795, EP2279182 and EP2155375 has been developed. Such guard bed systems typically comprise one or more guard bed vessels, each guard bed vessel comprising an inlet, an outlet and a packed bed ("guard bed") comprising an absorbent ("guard bed material") capable of reducing the quantity of iodide-containing impurities in a fluid stream by chemical or physical means including, but not limited to, reaction with the impurities and absorption of the impurities.

During operation, the guard beds become increasingly exhausted, and hence need to be refreshed by partially or entirely removing the guard bed material and replacing it with fresh or re-activated guard bed material. In a characteristic set-up, a first guard bed vessel is on-line while a second guard bed vessel is kept in stand-by and switched on as soon as the first guard bed needs to be refreshed, until the second guard bed (with the refreshed first bed stand-by) becomes exhausted and the process is repeated. Typically, in such a simple guard bed arrangement, the guard bed material is only partially used up when the amount of iodide-containing impurities passing through the guard bed vessel will already have risen to unacceptable levels. In an effort to enhance the utilization of expensive guard bed material, very recently more advanced guard bed system arrangements have been developed, wherein an iodide-contaminated gaseous stream is fed through a connected array of guard bed vessels, and wherein the first guard bed vessel in line upon becoming exhausted is refreshed and subsequently reinserted and used as the last guard vessel bed in line in a merry-go-round-like fashion as disclosed in co-pending European patent application 15200254.9.

In whichever arrangement, vigilant on-line monitoring of gaseous iodide levels is warranted, both for preventing the catastrophic incident of too high levels of organic iodides reaching the EO catalyst and for maximizing the utilization of guard bed material before it is replaced. Existing methods for determining organic halide concentrations include Gas Chromatography (GC). However, a Flame Ionization Detector (FID) as typically employed in such GC methods is merely capable of achieving detection limits in the order of 100 parts per billion by volume (ppbv) for organic iodides, which is more than three orders of magnitude higher than the desired target detection limit of about 20 parts per trillion by volume (pptv) for organic iodides. While in theory the latter resolution may be obtained using (off-line) Gas Chromatography-Mass Spectrometry (GC-MS) analysis, GC-MS methods are considered impractical for on-line analysis of gaseous process stream due to the complexity of the instrument, high maintenance requirements and lack of stability of calibration. Alternatively, a GC apparatus equipped with a Micro Electron Capture Detector (µECD) would be capable of detecting iodide concentrations down to several pptv, and would be preferred in terms of operational simplicity and stability over a mass spectral detector. However, contrary to Flame Ionization Detectors (FIDs), Micro Electron Capture Detectors (µECDs) exhibit a non-linear response to gaseous analyte concentrations, such as organic iodide concentrations in an EO conversion process, which necessitates the provision of reliable calibration curves for iodide concentrations in the preferred detection window of several parts per million down to the desired target detection limit of about 20 parts per trillion by volume (pptv). This requires feeding samples containing the gaseous analytes in different concentrations spanning the desired calibration range to the µECD-equipped GC apparatus, so as to obtain multi-point calibration curves covering the full required detection range. However, accurate gas calibration standards are only commercially available down to the 1000 to 2 ppmv concentration range. Thus, there is a need of reliable means for providing blends of commercial gas standards and inert diluent gas in controlled mixing ratios so as to serve as highly diluted calibration standards for detectors operating in the parts per billion volume (pptv) to parts per trillion volume (pptv) range.

Accordingly, it would be desirable to provide an improved method and system for blending gas standards with an inert diluent gas matrix to obtain diluted standard gas samples for use as calibration standards. It would further be desirable to provide an improved method for quantitatively analyzing a gaseous process stream comprising gaseous organic halides, particularly iodides and chlorides. The present inventors have sought to provide an integrated system for on-line analyzing organic halide impurity levels in gaseous process streams, in particular a system for on-line detection of gaseous organic halides, in particular iodides, in concentrations down to the parts per trillion by volume (pptv) range. The present inventors have further sought to provide an improved catalytic process for producing alkylene carbonate and/or alkylene glycol, preferably ethylene carbonate and/or ethylene glycol, as well as an improved method of reducing iodide impurities levels in such a process.

SUMMARY OF THE INVENTION

Accordingly, in one aspect, a gas blending system is provided wherein said gas blending system provides blends of a first gas and a second gas in different mixing ratios, said gas blending system comprising (a) means for separately controlling the flow rate and/or pressure of a first gas stream supplied to each of two or more flow restrictor devices arranged in parallel, wherein each flow restrictor device has an inlet for receiving and an outlet for discharging a stream of the first gas, wherein said outlet is fluidly connected to means for measuring the pressure of the first gas stream discharged from the flow restrictor device, and wherein the dimensions of the flow restrictor devices are selected such that each of said flow restrictor devices produces a different controlled volumetric flow rate of the first gas stream at the outlet, and (b) means for controlling the flow rate of a second gas stream supplied to a multi-port flow selector device, wherein said multi-port flow selector device comprises an inlet for receiving and outlets for removing a stream of the second gas at a controlled volumetric flow rate, (c) a mixing zone located downstream of each flow restrictor device and the multi-port flow selector device, wherein each mixing zone comprises a first inlet for receiving a stream of the first gas from the outlet of the flow restrictor device fluidly connected to it, a second inlet for receiving a stream of the second gas from an outlet of the multi-port flow selector device and an outlet for discharging a blend of the first gas and the second gas.

Typically, the first gas is a standard gas with known concentrations of components ("analytes") and the second gas is a diluent gas. By sequentially directing flow of standard gas to one of a set of at least two flow restrictor devices arranged in parallel, wherein said flow restrictor devices have different dimensions and yield different volumetric flow rates of the standard gas to a mixing chamber for mixing with inert diluent gas, it is possible to obtain a plurality of diluted standard gas samples having accurate analyte concentrations spanning multiple, overlapping concentration ranges for use in calibration of a suitable detector for a gaseous analyte. While it has been attempted previously to prepare highly diluted standard gas standards by serial, multi-step dilution of undiluted gas standard gas standards, the present disclosure provides a dynamic gas blending (dilution) method and associated system involving only a single dilution step per gas standard gas sample produced, even in the sub-ppbv concentration range.

Accordingly, in another aspect there is provided a method for calibrating a detector in an apparatus for quantitatively analyzing one or more components ("analytes") in a gaseous stream, said method comprising the steps of (i) providing a standard gas, wherein said standard gas contains each of the components to be analyzed in a fixed concentration, and an inert diluent gas;

(ii) feeding the standard gas and the diluent gas to a gas blending system to obtain a diluted standard gas sample having a known concentration;

(iii) feeding the diluted standard gas sample obtained in step (ii) to the analytical apparatus and recording a detector output for said sample;

(iv) repeating steps (ii) and (iii) at least twice in succession to obtain a series of diluted standard gas samples having different concentrations and corresponding detector outputs;

(v) combining the detector outputs for the diluted standard gas samples to generate a calibration curve for the detector, wherein said gas blending system comprises (a) means for controlling the flow rate or pressure of the standard gas supplied to two or more different flow restrictor devices arranged in parallel, wherein each flow restrictor device has an inlet for receiving and an outlet for discharging the standard gas, wherein said outlet is fluidly connected to means for measuring the pressure of the standard gas stream discharged from the flow restrictor device, and wherein the dimensions of the flow restrictor devices are selected such that each flow restrictor device produces a different controlled volumetric flow rate of the standard gas at the outlet, and (b) means for controlling the flow rate of a diluent gas supplied to a multi-port flow selector device, wherein said multi-port flow selector device comprises an inlet for receiving and outlets for removing the diluent gas at a controlled volumetric flow rate, (c) two or more mixing zones located downstream of the flow restrictor devices and the multi-port flow selector device, wherein each mixing zone comprises a first inlet for receiving standard gas from the outlet of the flow restrictor device fluidly connected to it, a second inlet for receiving diluent gas from an outlet of the multi-port flow selector device and an outlet for discharging a diluted standard gas sample, and wherein said series of diluted standard gas samples having different concentrations is obtained by using the multi-port flow selector device to selectively direct flow of the diluent gas to each of the mixing zones, and by successively adjusting the volumetric flow rate of the standard gas from the outlet of the flow restrictor device supplied to each mixing zone, and optionally adjusting the volumetric flow rate of the diluent gas supplied to each of the mixing zones, to produce a variety of mixing ratios of standard gas and diluent gas.

In another aspect, an in-line (or "on-line") analyzer for quantitatively analyzing a gaseous process stream is provided, said analyzer comprising (i) one or more inlets configured to receive a gaseous process stream withdrawn from one or more sample points of a chemical conversion system;

(ii) a gas system including (a) means for separately controlling the flow rate and/or pressure of a first gas stream supplied to each of two or more flow restrictor devices arranged in parallel, wherein each flow restrictor device has an inlet for receiving and an outlet for discharging a stream of the first gas, wherein said outlet is fluidly connected to means for measuring the pressure of the first gas stream discharged from the flow restrictor device, and wherein the dimensions of the flow restrictor devices are selected such that each of said flow restrictor devices produces a different controlled volumetric flow rate of the first pas stream at the outlet, and (b) means for controlling the flow rate of a second gas stream supplied to a multi-port flow selector device, wherein said multi-port flow selector device comprises an inlet for receiving and outlets for removing a stream of the second gas at a controlled volumetric flow rate, (c) a mixing zone located downstream of each flow restrictor device and the multi-port flow selector device, wherein each mixing zone comprises a first inlet for receiving a stream of the first gas from the outlet of the flow restrictor device fluidly connected to it, a second inlet for receiving a stream of the second gas from an outlet of the multi-port flow selector device and an outlet for discharging a blend of the first gas and the second gas, wherein the gas blending system is configured to prepare gas blends for use as calibration standard;

(iii) an analytical apparatus, wherein the analytical apparatus comprises one or more detectors that are sensitive to the components of the gaseous process stream to be analyzed.

Further, in accordance with another aspect of the present disclosure there is provided a method for quantitatively analyzing a gaseous process stream comprising one or more gaseous organic halides, said method comprising the steps of (i) withdrawing a sample of a gaseous process stream from one or more sample points in a chemical conversion process;

(ii) supplying the sample of a gaseous process stream to an analyzer including (i) one or more inlets configured to receive a gaseous process stream withdrawn from one or more sample points of a chemical conversion system: (ii) a pas blending system including (a) means for separately controlling the flow rate and/or pressure of a first gas stream supplied to each of two or more flow restrictor devices arranged in parallel, wherein each flow restrictor device has an inlet for receiving and an outlet for discharging a stream of the first gas, wherein said outlet is fluidly connected to means for measuring the pressure of the first gas stream discharged from the flow restrictor device, and wherein the dimensions of the flow restrictor devices are selected such that each of said flow restrictor devices produces a different controlled volumetric flow rate of the first gas stream at the outlet, and (b) means for controlling the flow rate of a second gas stream supplied to a multi-port flow selector device, wherein said multi-port flow selector device comprises an inlet for receiving and outlets for removing a stream of the second gas at a controlled volumetric flow rate (c) a mixing zone located downstream of each flow restrictor device and the multi-port flow selector device, wherein each mixing zone comprises a first inlet for receiving a stream of the first gas from the outlet of the flow restrictor device fluidly connected to it a second inlet for receiving a stream of the second gas from an outlet of the multi-port flow selector device and an outlet for discharging a blend of the first gas and the second gas, wherein the gas blending system is configured to prepare gas blends for use as calibration standard; (iii) an analytical apparatus, wherein the analytical apparatus comprises one or more detectors that are sensitive to the components of the gaseous process stream to be analyzed;

(iii) determining the concentration of the gaseous organic halides in the gaseous process stream sample, wherein prior to step (iii) the one or more detectors of the analytical apparatus of the analyzer have been calibrated for the gaseous organic halides to be analyzed.

As will be further disclosed herein below, the present invention allows continuous, on-line detection of gaseous organic iodides down to sub-ppbv levels, suitably to tens of pptv levels, and obviates the need for performing intermittent off-line testing using more complex and/or less sensitive analysis techniques.

The present analyzer and method for using said analyzer is particularly suited for monitoring iodide levels in a catalytic process for converting ethylene to ethylene oxide, and the subsequent conversion to ethylene carbonate and/or ethylene glycol, wherein the silver-based catalysts typically used in the ethylene epoxidation reactor are protected from poisoning by organic halides by the use of guard bed systems. By recurrently taking on-line samples from the process streams entering and leaving the one or more guard bed vessels and at other positions in the reaction system, it is possible not only to prevent any organic halides from poisoning the epoxidation catalyst, but also to recognize trends in halide production and guard bed capacity utilization, and make accurate predictions of guard bed breakthrough, thus maximizing guard bed utilization and minimizing associated operating expenses.

As will be described in more detail herein below, an advantageous aspect of the present disclosure is the use of a standard gas containing organic chlorides in large excess to iodides (e.g., a chloride to iodide molar ratio of about 1000:1), and using the linear signal response of the detector used for measuring the higher organic chloride concentrations, as a validation tool for the accuracy of the gas standard dilutions provided for calibration of the more sensitive, but non-linear, detector employed for measuring the iodide concentrations.

DETAILED DESCRIPTION OF THE INVENTION

Figure 1:
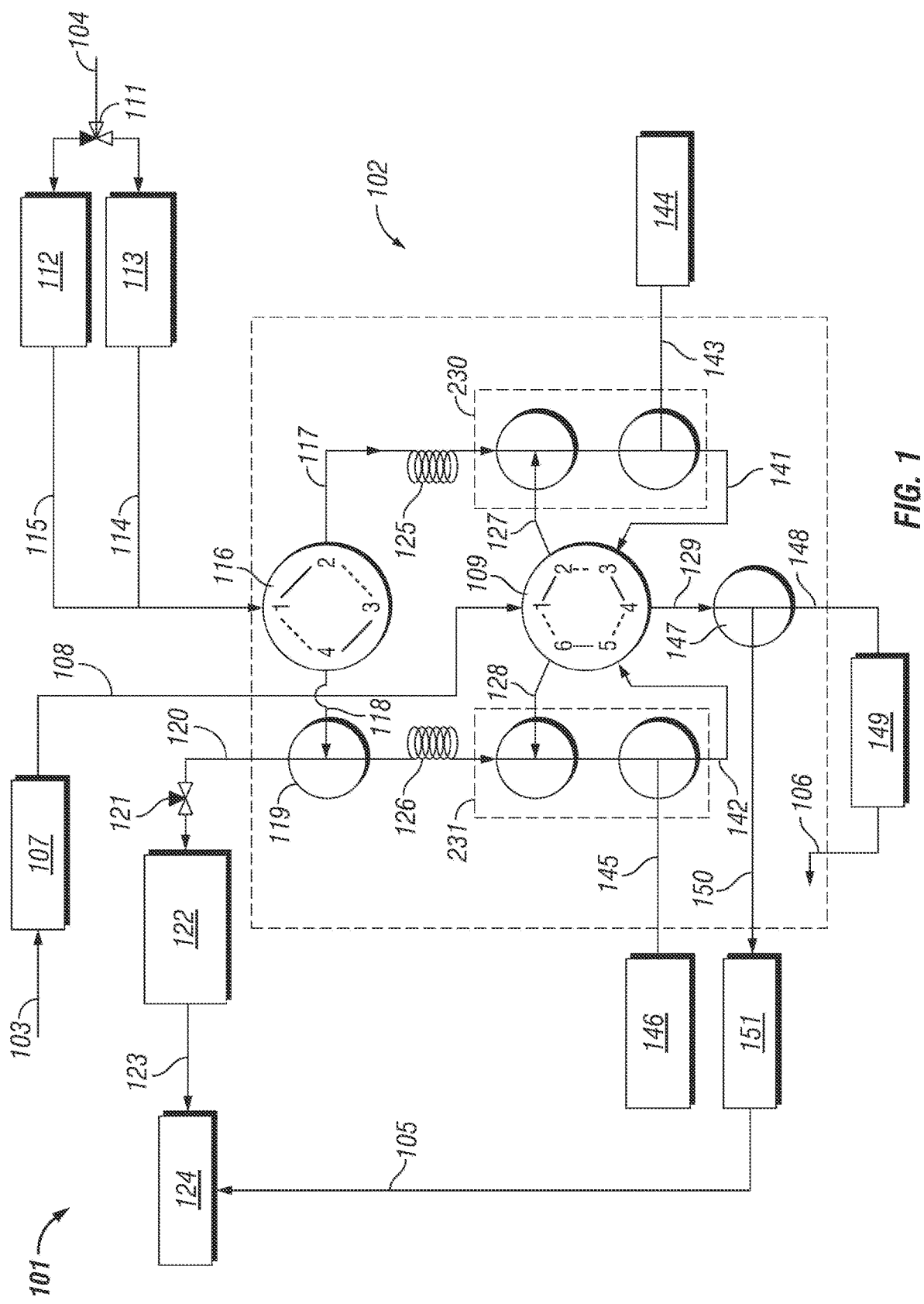
FIGS. 1 to 5 are schematic diagrams showing exemplary, but non-limiting embodiments of the invention.

Described herein are methods and associated systems for quantitatively analyzing a gaseous process stream comprising one or more gaseous organic halides. Such gaseous organic halides may be present as impurities in a recycle gas stream in a process for the production of ethylene carbonate and/or ethylene glycol.

The process of producing ethylene glycol and/or ethylene carbonate by epoxidation of ethylene and reactive absorption of ethylene oxide has been described in detail in, among others, WO2009021830, WO2009140318, WO2009140319, the disclosures of which are hereby incorporated by reference. Typically, the epoxidation process comprises reacting, in an ethylene epoxidation reactor, ethylene with oxygen in the presence of an epoxidation catalyst to form ethylene oxide. In such a reaction, the oxygen may be supplied as oxygen or as air, but is preferably supplied as oxygen. Ballast gas, for example methane or nitrogen, is typically supplied to allow operation at high oxygen levels without causing a flammable mixture. Moderator, e.g. monochloroethane (ethyl chloride), vinyl chloride or dichloroethane, may be supplied for ethylene oxide catalyst performance control, e.g. suppressing the undesirable oxidation of ethylene or ethylene oxide to carbon dioxide and water.

The ethylene epoxidation reactor is typically a multitubular, fixed bed reactor. The epoxidation catalyst preferably comprises silver and optionally promoter metals deposited on a support material, for example, alumina. The epoxidation reaction is preferably carried out at pressures of greater than 1 MPa and less than 3 Mpa and temperatures of greater than 200° C. and less than 300° C. The ethylene oxide product stream withdrawn from the ethylene epoxidation reactor is preferably cooled in one or more coolers, preferably with generation of steam at one or more temperature levels.

The ethylene oxide product stream from the ethylene epoxidation reactor, which typically comprises ethylene oxide, unreacted reactants (i.e., ethylene and oxygen), carbon dioxide, and water, is then passed to an absorber in which it is intimately contacted with lean absorbent. Typically, the lean absorbent comprises at least 20 wt % water, and preferably comprises from 20 wt % to 80 wt % water. The lean absorbent may also comprise ethylene glycol.

In the absorber, the ethylene oxide product stream is intimately contacted with the lean absorbent in the presence of one or more carboxylation and hydrolysis catalysts. If this occurs in the presence of only one catalyst, then the catalyst must promote carboxylation and hydrolysis. If this occurs in the presence of two or more catalysts, then each catalyst can promote carboxylation or hydrolysis or can promote both reactions (provided that at least one catalyst promotes carboxylation and at least one catalyst promotes hydrolysis). Preferably, the ethylene oxide product stream is contacted with lean absorbent in the presence of at least two catalysts including a first catalyst that promotes carboxylation and a second catalyst that promotes hydrolysis. Suitably, the absorber may be the sort of reactive absorber described in WO2009021830 or in co-pending application PCT/EP2015/071534.

Preferably, the one or more carboxylation and hydrolysis catalysts is/are homogenous, and the lean absorbent contains the one or more catalysts. Homogeneous catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenyl-propylphosphonium bromide, triphenylbenzylphosphonium chloride, tetraethylammonium bromide, tetramethyl-ammonium bromide, benzyltriethylammonium bromide, tetrabutylammonium bromide and tributylmethylammonium iodide. Preferred homogeneous catalysts that are known to promote carboxylation include alkali metal iodides such as potassium iodide and halogenated organic phosphonium or ammonium salts such as tributylmethylphosphonium iodide, tetrabutylphosphonium iodide, triphenylmethylphosphonium iodide and tributylmethylammonium iodide.

Homogeneous catalysts that are known to promote hydrolysis include basic alkali metal salts such as potassium carbonate, potassium hydroxide and potassium bicarbonate, or alkali metal metalates such as potassium molybdate. Preferred homogeneous catalyst systems include a combination of potassium iodide and potassium carbonate, and a combination of potassium iodide and potassium molybdate.

In another embodiment, the one or more carboxylation and hydrolysis catalysts is/are heterogeneous and the heterogeneous catalyst(s) is/are contained in vertically stacked trays. Heterogeneous catalysts that promote carboxylation include quaternary ammonium and quaternary phosphonium halides immobilized on silica, quaternary ammonium and quaternary phosphonium halides bound to insoluble polystyrene beads, and metal salts such as zinc salts immobilised on solid supports containing quaternary ammonium or quaternary phosphonium groups, such as ion exchange resins containing quaternary ammonium or quaternary phosphonium groups. Heterogeneous catalysts that promote hydrolysis include metalates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups.

The temperature in the absorber is preferably from 50° C. to 160° C., preferably from 80° C. to 150° C., more preferably from 80° C. to 120° C. This is higher than the temperature in an absorber in a conventional process and is required to promote the carboxylation and hydrolysis reactions. Temperature higher than 160° C. is not preferred as this may reduce the selectivity of ethylene oxide conversion to ethylene glycol. Both the ethylene oxide product stream and the lean absorbent are preferably supplied to the absorber at temperatures in the range from 50° C. to 160° C.

The pressure in the absorber is from 1 to 4 Mpa, preferably from 2 to 3 Mpa. The preferred pressure is a compromise between lower pressures that require less expensive equipment (e.g. equipment having thinner walls) and higher pressures that increase absorption and reduce the volumetric flow of the gas, thereby reducing the size of equipment and piping.

At least 50% of the ethylene oxide entering the absorber is converted in the absorber. Preferably, at least 60%, more preferably at least 70%, even more preferably at least 80%, most preferably at least 90% of the ethylene oxide entering the absorber is converted in absorber. The ethylene oxide may undergo carboxylation, providing ethylene carbonate. The ethylene oxide may undergo hydrolysis, providing ethylene glycol. Additionally, the ethylene carbonate that is produced from the ethylene oxide may undergo hydrolysis, providing ethylene glycol.

The ethylene oxide product stream supplied to the absorber comprises carbon dioxide. However, it is possible that the ethylene oxide product stream may contain insufficient carbon dioxide to achieve desired levels of carboxylation. Optionally, an additional source of carbon dioxide is supplied to the absorber, e.g. recycle carbon dioxide from a finishing reactor, carbon dioxide from a carbon dioxide recovery unit or, at start-up, carbon dioxide from an external source.

A 'fat absorbent' stream is withdrawn from the absorber, preferably by withdrawing liquid from the bottom of the absorber. The fat absorbent stream will comprise ethylene carbonate and/or ethylene glycol and any remaining ethylene oxide, if present, depending on the conditions, set-up and catalyst in the absorber. In addition, when the one or more carboxylation and hydrolysis catalysts is/are homogenous, the fat absorbent stream will further comprise the one or more carboxylation and hydrolysis catalysts.

Optionally, a portion or all of the fat absorbent stream is supplied to one or more finishing reactors (e.g., to provide further conversion of any ethylene oxide and/or ethylene carbonate that was not converted to ethylene glycol in the absorber). Suitable finishing reactors may include a carboxylation reactor, a hydrolysis reactor, a carboxylation and hydrolysis reactor, and a combination thereof. Supply to one or more finishing reactors is preferred if a significant quantity (e.g. at least 1%) of ethylene oxide or ethylene carbonate is not converted to ethylene glycol in the absorber. To maximize conversion of ethylene oxide in the absorber, spraying nozzles can be employed in the sump (bottom section) of the absorber, to disperse carbon dioxide and promote carboxylation. Optionally, steam may be injected into a finishing reactor suitable for hydrolysis.

Carbon dioxide may be produced in the one or more finishing reactors and, if desired, may be separated from the one or more finishing reactor product stream(s) as it leaves the one or more finishing reactors and is optionally recycled to the absorber.

The temperature in the one or more finishing reactors is typically from 100° C. to 200° C., preferably from 100° C. to 180° C. The pressure in the one or more finishing reactors is typically from 0.1 to 3 Mpa.

The fat absorbent stream or a finishing reactor product stream is optionally supplied to a flash vessel or to a light ends stripper. Light ends (e.g., gases such as ethylene, and also ballast gases such as methane) are removed in the flash vessel or in the light ends stripper. Optionally, if desired, flash vaporization may be achieved in a finishing reactor (e.g., hydrolysis reactor) so that a separate flash vessel may not be required and the equipment used in the process is thereby reduced. Optionally, a flash vessel may be located directly after the absorber so the fat absorbent stream passes directly from an outlet of the absorber to the flash vessel. When there is at least one finishing reactor, a flash vessel may be located after all of the one or more finishing reactors so that the finishing reactor product stream passes from said finishing reactors to the flash vessel. When there is more than one finishing reactor, a flash vessel may be located between the finishing reactors such that the fat absorbent stream passes from the absorber to at least one finishing reactor, then the finishing reactor product stream passes to the flash vessel and then the stream from the flash vessel passes to at least another finishing reactor. The flash can be at pressure from 0.01 to 2 Mpa, preferably from 0.1 to 1 Mpa, most preferably from 0.1 to 0.5 Mpa.

Gases that are not absorbed in the absorber are removed at or near the top of the absorber and condensed to yield an overhead absorber stream, which may be supplied to a vapor-liquid separator, such as a knock-out vessel, flash vessel, etc. A recycle gas stream, which typically comprises unreacted reactants (e.g., ethylene and oxygen), ballast gas (e.g., methane), carbon dioxide, etc., may be withdrawn from the vapor-liquid separator, typically at or near the top. Optionally, at least a portion of the recycle gas stream withdrawn from such a vapor-liquid separator is supplied to a carbon dioxide absorption column, wherein carbon dioxide is at least partially absorbed by a recirculating absorbent stream. An aqueous bottoms stream, which generally comprises water, one or more impurities and optionally glycols, is withdrawn from the vapor-liquid separator, typically at or near the bottom, and at least a portion of the aqueous bottoms stream may then be supplied to a distillation apparatus as an aqueous process stream. Optionally, if desired, a portion of the aqueous bottoms stream may bypass such distillations apparatus and be combined with a purified aqueous process stream withdrawn from the distillation apparatus and supplied to the absorber.

It has been found that the use of an iodide-containing carboxylation catalyst may lead to the formation of iodide-containing impurities in the recycle-gas stream. These gaseous iodide-containing impurities, particularly alkyl iodides and vinyl iodide, can poison the epoxidation catalyst in the epoxidation reactor, even in minute quantities. Treating the recycle gas stream by contacting the stream with one or more guard bed materials capable of at least partially absorbing such iodide-containing impurities can reduce the amount of such impurities in the recycle gas stream and thus protect the performance of the epoxidation catalyst, in particular the selectivity and/or activity of the catalyst, as well as the duration of time the epoxidation catalyst can remain in the epoxidation reactor before it becomes necessary to exchange the catalyst with fresh epoxidation catalyst.

Suitably, the one or more guard beds may be the sort of guard beds and guard bed systems described in EP2285795, EP2279182 and EP2155375, as well as in co-pending applications EP15200254.9, EP15200267.1, EP15200272.1 and EP15200275.4, the disclosures of which are hereby incorporated by reference.

In using such guard beds and associated guard bed systems, the amount of gaseous iodide-containing impurities present in a recycle gas stream can be reduced to the very low levels the present inventors have found to be required for the performance of the epoxidation catalyst to remain substantially unaffected by its presence. In particular, the amount of alkyl iodide present in a (partially) treated recycle gas stream is preferably no more than 6 ppbv, more preferably no more than 5 ppbv, even more preferably no more than 3 ppbv, even more preferably no more than 2 ppbv, and most preferably no more than 1 ppbv. Further, the amount of vinyl iodide present in a treated recycle gas stream is preferably no more than 20 ppbv, preferably no more than 15 ppbv, preferably no more than 10 ppbv, more preferably no more than 5 ppbv, even more preferably no more than 4 ppbv, even more preferably no more than 3 ppbv, and most preferably no more than 1 ppbv. Similarly, the total amount of alkyl iodide and vinyl iodide present in a treated recycle gas stream supplied to the epoxidation reactor is preferably no more than 26 ppbv, preferably no more than 20 ppbv, preferably no more than 16 ppbv, preferably no more than 13 ppbv, preferably no more than 10 ppbv, more preferably no more than 7 ppbv, even more preferably no more than 5 ppbv, most preferably no more than 2 ppbv.

Thus, in accordance with the present disclosure, an analyzer and a method are provided that allow the continuous and accurate detection of such very low levels of gaseous iodide-containing impurities present in a recycle gas stream of a processes for producing ethylene carbonate and/or ethylene glycol. In further accordance with the present disclosure, a method for calibrating such an analyzer and a gas blending system that allows the preparation of highly diluted calibration standards are provided.

Accordingly, in one aspect the present disclosure pertains to a gas blending system, wherein said gas blending system provides blends of a first gas and a second gas in different mixing ratios, said gas blending system comprising
(a) means for separately controlling the flow rate and/or pressure of a first gas stream supplied to each of two or more flow restrictor devices arranged in parallel, wherein each flow restrictor device has an inlet for receiving and an outlet for discharging a stream of the first gas, wherein said outlet is fluidly connected to means for measuring the pressure of the first gas stream discharged from the flow restrictor device, and wherein the dimensions of the flow restrictor devices are selected such that each of said flow restrictor devices produces a different controlled volumetric flow rate of the first gas stream at the outlet, and
(b) means for controlling the flow rate and/or pressure of a second gas stream supplied to a multi-port flow selector device, wherein said multi-port flow selector device comprises an inlet for receiving and outlets for removing a stream of the second gas at a controlled volumetric flow rate,
(c) a mixing zone located downstream of each flow restrictor device and the multi-port flow selector device, wherein each mixing zone comprises a first inlet for receiving a stream of the first gas from the outlet of the flow restrictor device fluidly connected to it, a second inlet for receiving a stream of the second gas from an outlet of the multi-port flow selector device and an outlet for discharging a blend of the first gas and the second gas.

In one embodiment, the first gas is a standard gas containing one or more chemical compounds in known absolute concentrations, while the second gas is an inert gas (or a mixture of inert gases). Thus, in one embodiment, the gas blending system is employed to provide blends (mixtures) of a standard gas and a diluent gas in a number of different mixing ratios, wherein said blends serve as dilute calibration standards for an analytical apparatus. The diluent gas is an inert gas that is capable of being mixed with the standard gas in all molar ratios, such as nitrogen, argon or helium. Preferably, nitrogen is used as diluent gas.

Suitable means for measuring the pressure of the first gas stream discharged from the flow restrictor device, i.e. pressure sensors, pressure transducers, pressure transmitters, piezometers, manometers etc. are known to the skilled person. In order to be able to accurately program or calculate the flows in the flow restrictor devices, it is preferred to locate the gas blending system in a controlled temperature zone.

In one embodiment, the blending system further comprises means for selectively splitting off a portion of the first gas stream supplied to a flow restrictor device, said means comprising a branched tubular body arranged upstream of the flow restrictor device, wherein said branched tubular body comprises an inlet for receiving the first gas stream, a first outlet connected to the flow restrictor device and a second outlet connected to an apparatus capable of metered venting of a portion of the first gas stream. This metered venting of a portion of the first gas stream allows maintaining sufficient pressure at very low flow rates of the first gas stream, if required.

Reference is now made to FIG. 1, which is a schematic view of gas blending system (101) according to an embodiment of the present disclosure. Gas blending system (101) generally comprises an oven (102), gas inlet lines (103) and (104) for supplying diluent gas and halide standard gas, respectively, as well as outlet lines (105) and (106) for withdrawing diluted halide standard gas. It will be clear to the skilled person, that as schematic diagrams, these figures do not show all necessary inputs, outputs, recycle streams, etc. that may be present in the reaction system. Furthermore, in the figures herein, as will be appreciated, elements can be added, exchanged, and/or eliminated so as to provide any number of additional embodiments and the sequence in which various streams are introduced into the process and their respective points of introduction, as well as the flow connections, may be varied from that depicted. In addition, as will be appreciated, the proportion and the relative scale of the elements provided in the figure are intended to illustrate the embodiments of the present disclosure, and should not be taken in a limiting sense.

As shown in FIG. 1, diluent gas may be supplied via inlet (103) to mass flow controller (107), which controls the flow rate of diluent gas through feed line (108) and supplied to port (P1) of 6-port valve (109). Halide standard gas may be supplied via feed line (104) to valve (111) for selecting halide standard gas flow to either mass flow controller (112) or forward pressure controller (113), which may be used to control mass flow or pressure, respectively, of halide standard gas supplied via feed line (115) or (114), respectively, to port 1 of 4-port valve (116). 4-port valve (116) further comprises ports (P2) and (P4) for supplying, either through line (117) or through line (118), optionally via tee connector (119), halide standard gas to flow restrictor device (125) or (126), respectively, which are in fluid communication with high-concentration mixing zone (230) and low-concentration mixing zone (231), respectively. Tee connector (119) is further fluidly connected via line (120) and through valve (121) to low-flow (2-10 sccm) mass flow controller (122), which is fluidly connected via line (123) to low-pressure vent header (124).

Figure 2:
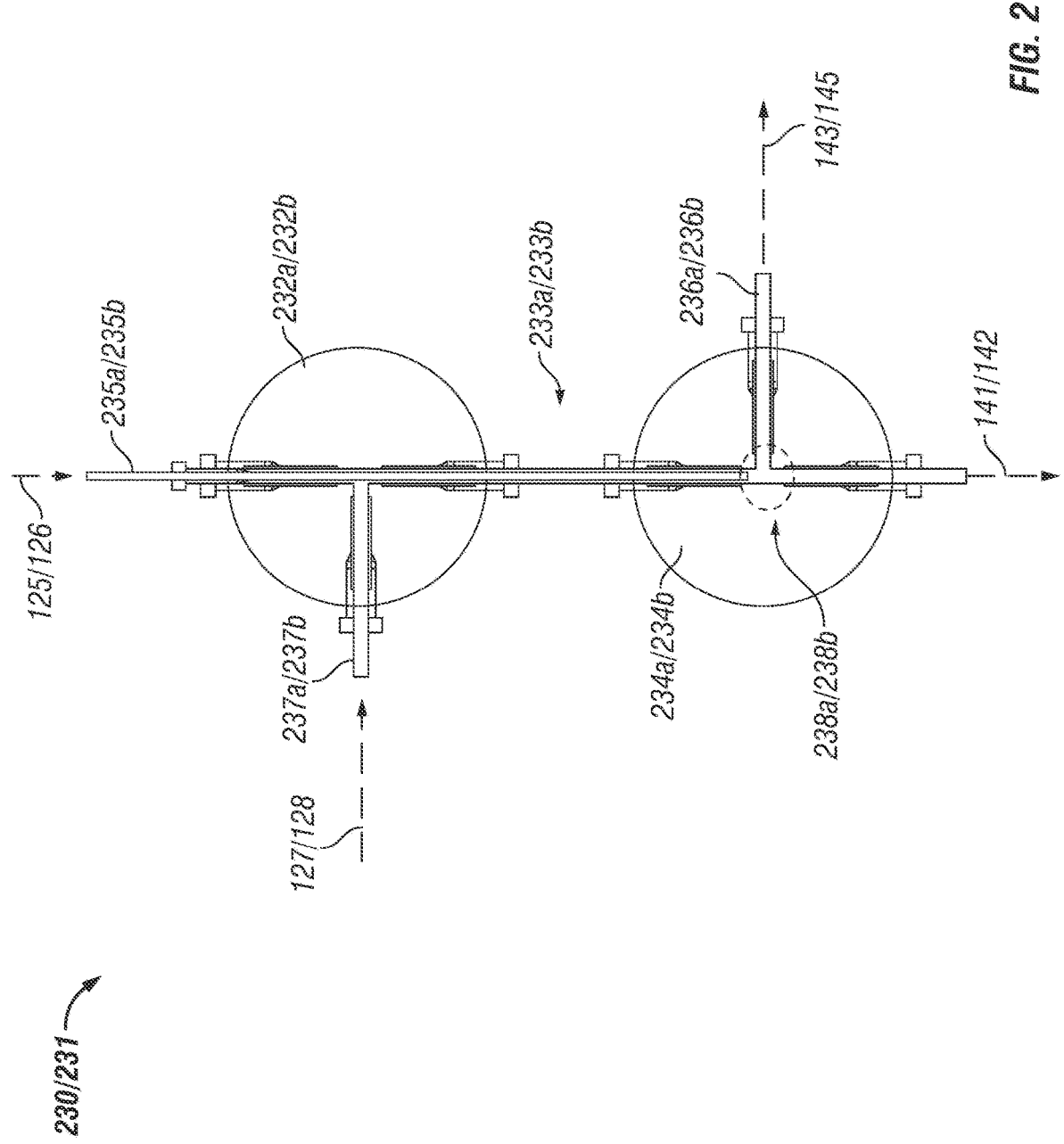

Mixing zones (230) and (231), details of which are exemplified in FIG. 2, each generally comprise an inlet for receiving halide standard gas through flow restrictor device (125) or through flow restrictor device (126), an inlet for receiving diluent gas via either line (127) or line (128) from port (P2) or port (P6) of 6-port valve (109), respectively, an outlet for supplying diluted halide standard through line (141) or line (142) to port (P3) or port (P5), respectively, of 6-port valve (109), and an outlet fluidly connected via line (143) or line (145) to pressure transducer (144) or (146), respectively.

Figure 4:
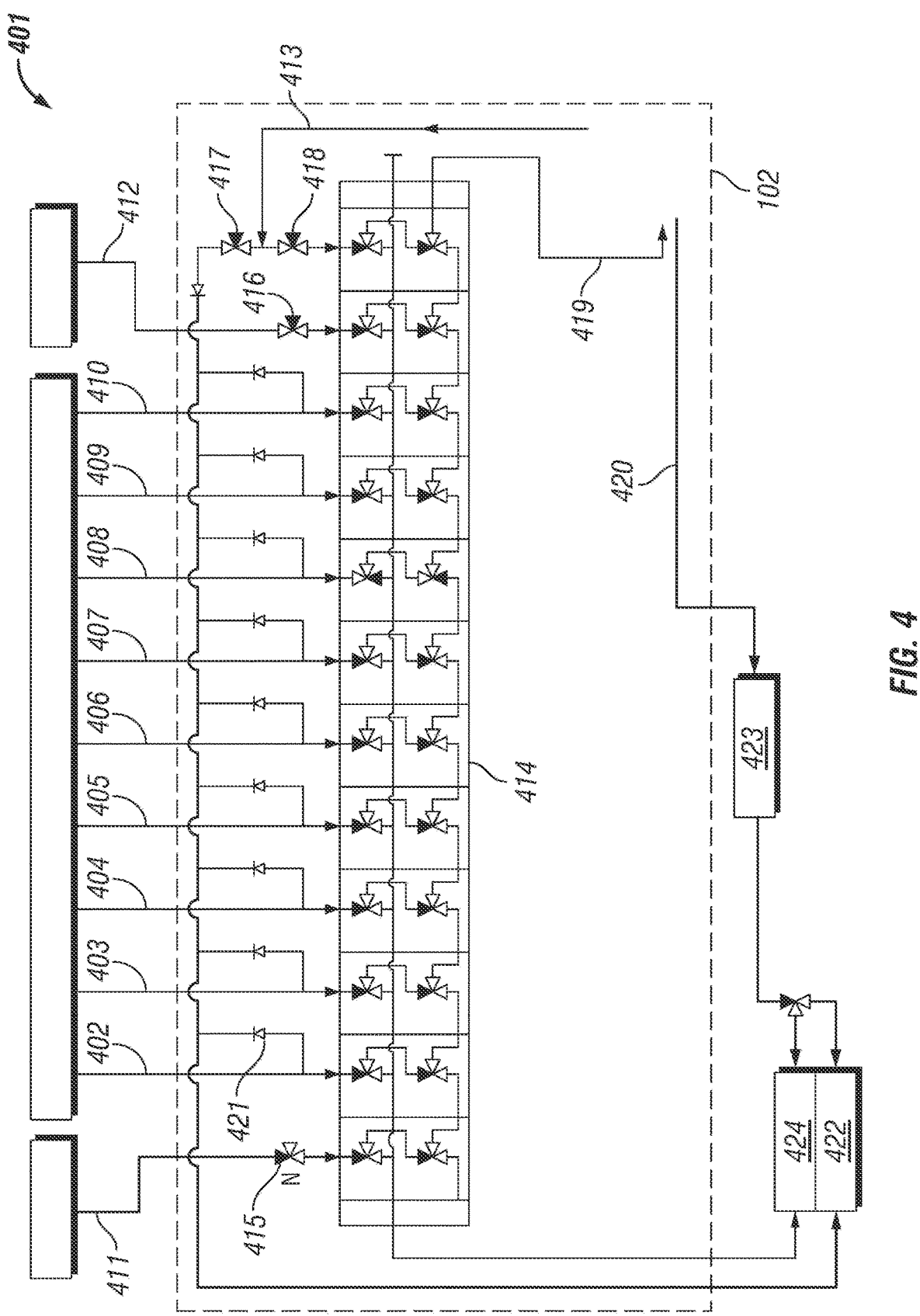

Port (P4) of 6-port valve (109) is configured to supply diluted halide standard gas suitable for use as calibration standard via line (129) through tee connector (147) and line (148) to mass flow controller (149), which may be in fluid communication through outlet (106) with a stream selection system (401), as depicted in FIG. 4. Tee connector (147) is fluidly connected through line (150) with back-pressure controller (151), which is fluidly connected through line (105) with low-pressure vent header (124).

FIG. 2 is a schematic view of mixing zones (230) and (231) referred to in FIG. 1 and generally in the present disclosure, wherein mixing zone (230) is configured to provide gas blends with concentrations that are relatively higher than those provided in mixing zone (231). Each of mixing zones (230) and (231) comprises two tee connectors (232a/232b) and (234a/234b) connected together with stainless steel tubing (233a/233b). Halide standard gas may be supplied (through either flow restrictor device (125) or flow restrictor device (126) depicted in FIG. 1) via capillary (235a/235/b), which is inserted fully through first tee connector (232a/232b) and positioned such that it ends just above branch (236a/236b) of second tee connector (234a/234b). Diluent gas may be supplied through either line (127) or line (128) via branch (237a/237b) of first tee connector (232a/232b) and flow around capillary (235a/235b), and subsequently be blended with halide standard gas in the space (238a/238b) adjacent branch (236a/236b) of second tee connector (234a/234b). Diluted halide standard gas can exit mixing zone (230) or (231) via branch (236a/236b) of tee connector (234a/234b) and be supplied through line (141) or (142) to port (P3) or (P5) of 6-port valve (109), depicted in FIG. 1, respectively. Branch (236a/236b) of second tee connector (234a/234b) is fluidly connected via line (143) or (145) to pressure transducer (144) or (146), respectively, depicted in FIG. 1, for measuring the exit pressures of flow restrictor devices (125) and (126), respectively.

The mixing zones of the gas blending system as described herein are generally known and used according to standard practice in the art. In the gas blending system and encompassed mixing zones illustrated in FIG. 1 and FIG. 2, the tubing connectors are tee connectors; these could however also be a Y-fitting or any other plural port configuration. Likewise, the 4-port and 6-port valves referred to in FIG. 1 may suitably be any multi-port switching valve capable of directing gas flows as described herein.

The gas blending system as disclosed herein, such as gas blending system (101), is typically operated using operating software that controls diluent gas mass flow controller (107), valve (111), halide standard mass flow controller (112), forward pressure controller (113), 4-port valve (116), 6-port valve (109), low-flow mass flow controller (122), pressure transducer (144) or (146), mass flow controller (149) and back-pressure controller (151).

In accordance with one embodiment of the present invention, mixing zones (230) and (231) are configured such that one mixing zone allows blending of relatively high concentration calibration standards (e.g., 1-1000 ppmv chlorides, 1-1000 ppbv iodides) and one mixing zone is capable of blending low concentration calibration standards (e.g., 0.02-50 ppmv chlorides, 0.02-50 ppbv iodides). This is suitably achieved by selecting the dimensions of the flow restrictor devices, e.g. flow restrictor device (125) or (126) as depicted in FIG. 1, such that each of said flow restrictor devices produces a different controlled volumetric flow rate of the first gas stream, in this case the halide standard gas, at the outlet of said flow restrictor device.

As used herein, the term flow restrictor device refers to any suitable device that is capable of restricting the flow of gas to a precisely metered rate. In one preferred embodiment of the present disclosure, the two or more flow restrictor devices are capillary flow restrictors. In capillary flow restrictors, the rate of volumetric flow through the capillary has a well-defined relation to the length and diameter of the capillary, and to the difference in pressure between the capillary inlet and the capillary outlet. More specifically, the volumetric flow rate Q through the capillary is given by the compressible Poiseuille flow equation:

$$Q_{SATP} = \frac{T_{Std}}{T} \frac{\pi R^4}{16 \mu L} \frac{(P_1^2 - P_2^2)}{P_{Std}} = \frac{C_o}{\mu T}(P_1^2 - P_2^2)$$

Herein:

$Q$ = volumetric flow rate (m$^3$/s)

$T_{Std}$ = standard ambient temperature (298.15 K)

$T$ = temperature (K)

$P_1$ = inlet pressure (bar)

$P_2$ = outlet pressure (bar)

$P_{Std}$ = standard ambient pressure (1 bar)

$R$ = capillary radius (m)

$L$ = capillary length (m)

$\mu$ = calculated gas blend viscosity (Pa s)

$$C_o = \frac{T_{Std}}{P_{Std}} \frac{\pi R^4}{16L} = \text{capillary constant}$$

The viscosity μ of the gas blend can be calculated using the equations derived in *A Simple and Accurate Method for Calculating Viscosity of Gaseous Mixtures*, Thomas A. Davidson, Report of investigations 9456 (United States. Bureau of Mines), 1993.

As can be seen, the volumetric flow rate through the capillary is proportional to the 4$^{th}$ power of capillary radius R (or diameter D) and is inversely proportional to capillary length (i.e., Q ∝R$^4$/L or Q ∝D$^4$/L). Accordingly, the volumetric flow rate of halide standard gas may be set at desired values by choosing capillary restrictors having suitable and different lengths and/or diameters and adjusting the flow rate at the capillary inlet and/or adjusting the pressure difference over said capillary. Thus, advantageously, the use of at least a first and a second capillary flow restrictor arranged in parallel, wherein said capillary flow restrictors have different (length L and/or diameter D) dimensions, allows obtaining diluted gas samples having accurate analyte concentrations spanning multiple, preferably overlapping concentration ranges for use in calibration of the detectors of the analytical apparatus used for determining analyte concentrations, such as GC detectors. By employing capillary flow restrictors having carefully selected dimension as flow restrictors for the standard gas to be blended with an inert diluent gas matrix, such as nitrogen, argon, or helium, it is possible to effectively obtain a series of highly diluted standard gas samples in only one dilution step, rather than several consecutive steps, per gas standard concentration produced. Suitable capillary flow restrictors and their dimensions will be apparent to those of ordinary skill in the art and are to be considered within the scope of the present disclosure. Typically, such flow restrictors are made of quartz or silica.

As an example, the gas blending system may use a capillary flow restrictor with nominal dimensions 10 m (L)×0.200 mm internal diameter (ID) (R=0.100 mm) for providing relatively high concentration gas blends, and a capillary flow restrictor with nominal dimensions 30 m×0.100 mm ID (R=0.050 mm) for providing relatively low concentration gas blends.

In accordance with one embodiment of the present disclosure, the gas blending system as disclosed herein is employed to provide calibration gas samples of nominal concentration by setting the required operating parameters (diluent flow, standard gas pressure difference over flow restrictor) for each concentration and determining the actual concentrations by acquiring relevant additional parameters (such as temperature) and calculating the flow rate of the standard gas using the compressible Poiseuille flow equation as provided above. In a preferred embodiment, the gas blending system as disclosed herein is employed to provide calibration gas samples comprising both organic chlorides and iodides.

With reference to FIG. 1, in use, in order to prepare high concentration gas blends (e.g., 1-1000 ppmv chlorides; 1-1000 ppbv iodides), diluent gas is supplied via inlet (103) to mass flow controller (107) in order to control the flow rate of diluent gas supplied through feed line (108) to port (P1) of 6-port valve (109). Halide standard gas of known concentration is supplied through inlet (104). Valve (111) is switched in order to supply calibration standard to forward pressure controller (113), which controls the pressure of calibration standard via feed line (114) to port 1 of 4-port valve (116). 4-port valve (116) is switched to provide flow of halide standard gas through line (117), which then proceeds through flow restrictor device (125) to high-concentration mixing zone (230). 6-port valve (109) is switched to supply diluent gas through line (127) to mixing zone (230), and the resulting diluted standard gas is supplied through line (141) to 6-port valve (109). Diluted standard gas suitable for use as calibration standard flows from port (P3) to port (P4) of 6-port valve (109), and passes through line (129), tee connector (147) and line (148) to mass flow controller (149), which sets the calibration gas flow to the stream selection system and sample loops. In this configuration, the inlet pressure to the flow restrictor device (125) is controlled with forward pressure controller (113), the exit pressure is set in the desired range (e.g., 1.6 bara) using back-pressure controller (151), while pressure transducer (144) measures the actual pressure at the exit of flow restrictor device (125).

In order to prepare low concentration gas blends (e.g., 0.02-50 ppmv chloride; 0.02-50 ppbv iodide), diluent gas is supplied via inlet (103) to mass flow controller (107) in order to control the flow rate of diluent gas supplied through feed line (108) to 6-port valve (109). Calibration standard is supplied through inlet (104). Valve (111) is switched in order to supply calibration standard to forward pressure controller (113), which controls the pressure of calibration standard supplied through feed line (114) to 4-port valve (116). 4-port valve (116) is switched to provide flow of halide standard gas through line (118), via tee connector (119), to flow restrictor device (126). When very low halide standard flow rates are desired, a portion of halide standard gas controlled by low-flow (2-10 sccm) mass flow controller (122) is allowed, via valve (121), to vent to low-pressure vent header (124). In this way, the total flow provided by forward pressure controller (113) is the sum of the flow supplied to flow restrictor device (126) and the split flow through line (120) and mass flow controller (122), which allows forward pressure controller (113) to maintain stable low pressure even at very low desired halide standard flow rates.

The halide standard proceeds through flow restrictor device (126) to low-concentration mixing zone (231). 6-port valve (109) is switched to supply diluent gas through line (128) to mixing zone (231), and the resulting diluted standard gas is supplied through line (142) to 6-port valve (109). Diluted standard gas suitable for use as calibration standard flows from port (P5) to port (P4) of 6-port valve (109), and passes through line (129), tee connector (147) and line (148) to mass flow controller (149), which sets the calibration gas flow to the stream selection system and sample loops. In this configuration, the inlet pressure to the flow restrictor device (126) is controlled with forward pressure controller (113), the exit pressure is set in the desired range (e.g., 1.6 bara) using back-pressure controller (151), while pressure transducer (146) measures the actual pressure at the exit of flow restrictor device (126).

For calibrating flow restrictor devices (125) and (126), i.e., determining the actual parameter $R^4/L$ of said devices (e.g., capillary restrictors), metered amounts of gas may be supplied through mass flow controller (112) and line (115) to the mixing zones via 4-port valve (116). The inlet and outlet pressures of the flow restrictor devices are measured using pressure reading from forward pressure controller (113) and pressures from either pressure transducer (144) or (146), and the Poiseuille equation (see above) is solved to obtain the value of $R^4/L$ for each restrictor.

The calibration gas samples with different concentration obtained using the gas blending system as disclosed herein can be employed to calibrate an analytical apparatus comprising one or more detectors that are sensitive to one or more components of the calibration standard.

More specifically, a benefit of the present disclosure is that it allows dilution of a standard gas having known concentrations of organic halide analytes, notably organic iodides comprising one or more of methyl iodide, ethyl iodide and vinyl iodide, to concentrations below the parts per million by volume concentration. Thus, in a preferred embodiment, the gas blending method as described herein is used to provide standard gas standards wherein the concentrations of the one or more individual iodides are below 100 parts per trillion by volume (pptv), preferably below 50 parts per trillion by volume (pptv), more preferably around 20 parts per trillion by volume (pptv). Advantageously, the provision of such diluted gas calibration standards allows providing multipoint calibration curves for gaseous organic iodide concentrations comprising one or more concentration points below 100 parts per trillion by volume (pptv), preferably below 50 parts per trillion by volume (pptv), more preferably around or below 20 parts per trillion by volume (pptv).

Accordingly, in one aspect, the present disclosure relates to a method for calibrating a detector in an analytical apparatus for quantitatively analyzing one or more components in a gaseous stream, comprising the steps of
(i) providing a standard gas, wherein said standard gas contains each of the components to be analyzed in a fixed concentration, and an inert diluent gas;
(ii) feeding the standard gas and the diluent gas to a gas blending system as disclosed herein to obtain a diluted standard gas sample having a known concentration;
(iii) feeding the diluted standard gas sample obtained in step (ii) to the analytical apparatus and recording a detector output for said sample;
(iv) repeating steps (ii) and (iii) at least twice in succession to obtain a series of diluted standard gas samples having different concentrations and corresponding detector outputs;
(v) combining the detector outputs for the diluted standard gas samples to generate a calibration curve for the detector,
wherein said series of diluted standard gas samples having different concentrations is obtained by
using the multi-port flow selector device to selectively direct flow of the diluent gas to each of the mixing zones, and by
successively adjusting the volumetric flow rate of the standard gas from the outlet of the flow restrictor device supplied to each mixing zone and
optionally adjusting the volumetric flow rate of the diluent gas supplied to each of the mixing zones,
to produce a variety of mixing ratios of standard gas and diluent gas.

In another aspect, the present disclosure relates to an analyzer for quantitatively analyzing the composition of a gaseous process stream, said analyzer comprising
(i) one or more inlets configured to receive a gaseous process stream withdrawn from one or more sample points of a chemical conversion system;
ii) a gas blending system including (a) means for separately controlling the flow rate and/or pressure of a first gas stream supplied to each of two or more flow restrictor devices arranged in parallel, wherein each flow restrictor device has an inlet for receiving and an outlet for discharging a stream of the first gas, wherein said outlet is fluidly connected to means for measuring the pressure of the first gas stream discharged from the flow restrictor device, and wherein the dimensions of the flow restrictor devices are selected such that each of said flow restrictor devices produces a different controlled volumetric flow rate of the first gas stream at the outlet, and (b) means for controlling the flow rate of a second gas stream supplied to a multi-port flow selector device, wherein said multi-port flow selector device comprises an inlet for receiving and outlets for removing a stream of the second gas at a controlled volumetric flow rate, (c) a mixing zone located downstream of each flow restrictor device and the multi-port flow selector device, wherein each mixing zone comprises a first inlet for receiving a stream of the first gas from the outlet of the flow restrictor device fluidly connected to it, a second inlet for receiving a stream of the second gas from an outlet of the multi-port flow selector device and an outlet for discharging a blend of the first gas and the second gas, wherein the gas blending system is configured to prepare gas blends for use as calibration standard;
(iii) an analytical apparatus, wherein the analytical apparatus comprises one or more detectors that are sensitive to the components of the gaseous process stream to be analyzed.

Preferably, the analyzer further comprises (iv) a stream selection system configured to selectively direct samples of the gaseous process stream and of the calibration standard gas blend to an analytical apparatus. Such a stream selection system may be any system comprising a plurality of inlets, outlets and valves that is capable of selectively receiving and discharging process stream samples, calibration standard and quality analysis (QA) samples, and gas purge streams.

In accordance with one embodiment of the present disclosure, the standard gas—and consequently the diluted calibration standards, too—comprises one or more analytes in a relatively low (known) concentration and one or more analytes in a relatively high (known) concentration. In conjunction with this embodiment, the analytical apparatus for measuring the concentration of these analytes may contain a detector that is configured to detect relatively high (known) concentrations of gaseous compounds and a detector that is configured to detect relatively low (known) concentrations of gaseous compounds. In some embodiments, the latter detector for detecting relatively low (known) concentrations of gaseous compounds may have a non-linear response to analyte concentration.

For example, in one embodiment the standard gas and the diluted calibration standards comprises analytes wherein the molar ratio of high-concentration analytes to low-concentration analytes is at least 100:1, preferably at least 500:1 more preferably about 1000:1. The use of a standard gas, and of its subsequent dilutions, having such a ratio of high-concentration analytes to low-concentration analytes allows validation of the calibration of a detector having non-linear response to very low analyte concentrations (such as a µECD), by verifying the linearity of response to high analyte concentrations in the same calibration standards of a detector with recognized linear response (such as an FID). In other words, if a linear dependence of detector (e.g., FID) response on high-concentration analytes is obtained for all dilutions prepared, this is an excellent indicator that the concentrations of the low-concentration analytes in the calibration standards provided to the detector (e.g., µECD) for acquiring low-concentration calibrations are also accurate, despite the fact that they are too low to straightforwardly measure or validate by any other technique. Accordingly, in a preferred embodiment of the present disclosure, the standard gas, and consequently the diluted calibration standards, comprise one or more organic chlorides and one or more organic iodides, wherein the molar ratio of organic chlorides to organic iodides is at least 100:1, preferably at least 500:1 more preferably about 1000:1. Preferably, the molar ratio of organic chlorides to organic iodides is at most 20,000:1, more preferably at most 10,000:1, and most preferably at most 5,000:1. For example, a standard gas comprising 2000 ppmv of each of methyl chloride, ethyl chloride and vinyl chloride, and 2000 ppbv (2 ppmv) of each of methyl iodide, ethyl iodide and vinyl iodide may be used to prepare calibration standards in a range of dilutions. The use of a standard gas, and of its subsequent dilutions, having this chloride to iodide ratio allows validation of the calibration of a detector having non-linear response to iodide concentrations (such as a µECD), by verifying the linearity of response to chloride concentrations in the same calibration standards of a detector with recognized linear response (such as an FID). In other words, if a linear dependence of detector (e.g., FID) response on chloride concentration is obtained for all dilutions prepared, this is an excellent indicator that the concentrations of the iodide gas standards provided to the detector (e.g., µECD) for acquiring iodide calibrations are also accurate, despite the fact that they are too low to straightforwardly measure or validate by any other technique.

In one embodiment, the analytical apparatus is a gas chromatography (GC) apparatus. Preferably, such apparatus is equipped with at least one detector that is sensitive to organic halide concentrations in the parts per trillion volume (pptv) range. Advantageously, the analytical apparatus comprises a first detector that is sensitive to organic halide concentrations down to several pptv. Preferably, this first detector is a Micro Electron Capture Detector (µECD). Advantageously, the analytical apparatus comprises a second detector that is sensitive to organic halide concentrations in the 10 ppbv to 1000 ppmv range. Preferably, this detector is a Flame Ionization Detector (FID). In a preferred embodiment, the analytical apparatus is a gas chromatography (GC) apparatus equipped with Micro Electron Capture Detector (µECD) and a Flame Ionization Detector (FID). Advantageously, a dual channel GC apparatus is used wherein iodides are detected by a µECD on the front channel and chlorides and/or other halides except iodides are detected by an FID on the back channel. Thus, in a preferred embodiment, the analyzer for quantitatively analyzing the composition of a gaseous process stream according to the present disclosure comprises, as the analytical apparatus, a gas chromatography (GC) apparatus equipped with Micro Electron Capture Detector (µECD) and a Flame Ionization Detector (FID), wherein iodides in the gaseous process stream are detected by the µECD and chlorides and/or other halides except iodides are detected by the FID. In another preferred embodiment, the method for calibrating a detector in an analytical apparatus for quantitatively analyzing one or more components in a gaseous stream as disclosed herein comprises feeding diluted standard gas samples to an analytical apparatus and recording a detector output for each sample, wherein the analytical apparatus is a gas chromatography (GC) apparatus equipped with a detector having non-linear response to low-concentration components in the calibration standard and a detector having a linear response to high-concentration components in the calibration standard, wherein the linear response of the detector having a linear response to high-concentration components is used to verify, i.e., validate, the accuracy of the calibration of the detector having a non-linear response to low-concentration components. Thus, in a preferred embodiment of the method for calibrating a detector in an analytical apparatus for quantitatively analyzing one or more analytes in a gaseous stream as disclosed herein, the analytical apparatus comprises a first detector with non-linear response to analyte concentration and a second detector with linear response to analyte concentration, wherein the analyte concentrations detected by the first detector are lower than the analyte concentrations detected by the second detector and wherein a linear response of the second detector is used to validate the accuracy of the calibration of the first detector. In one embodiment, the detector having a non-linear response is a Micro Electron Capture Detector (µECD). In one embodiment, the detector having linear response is a Flame Ionization Detector (FID).

Figure 3:
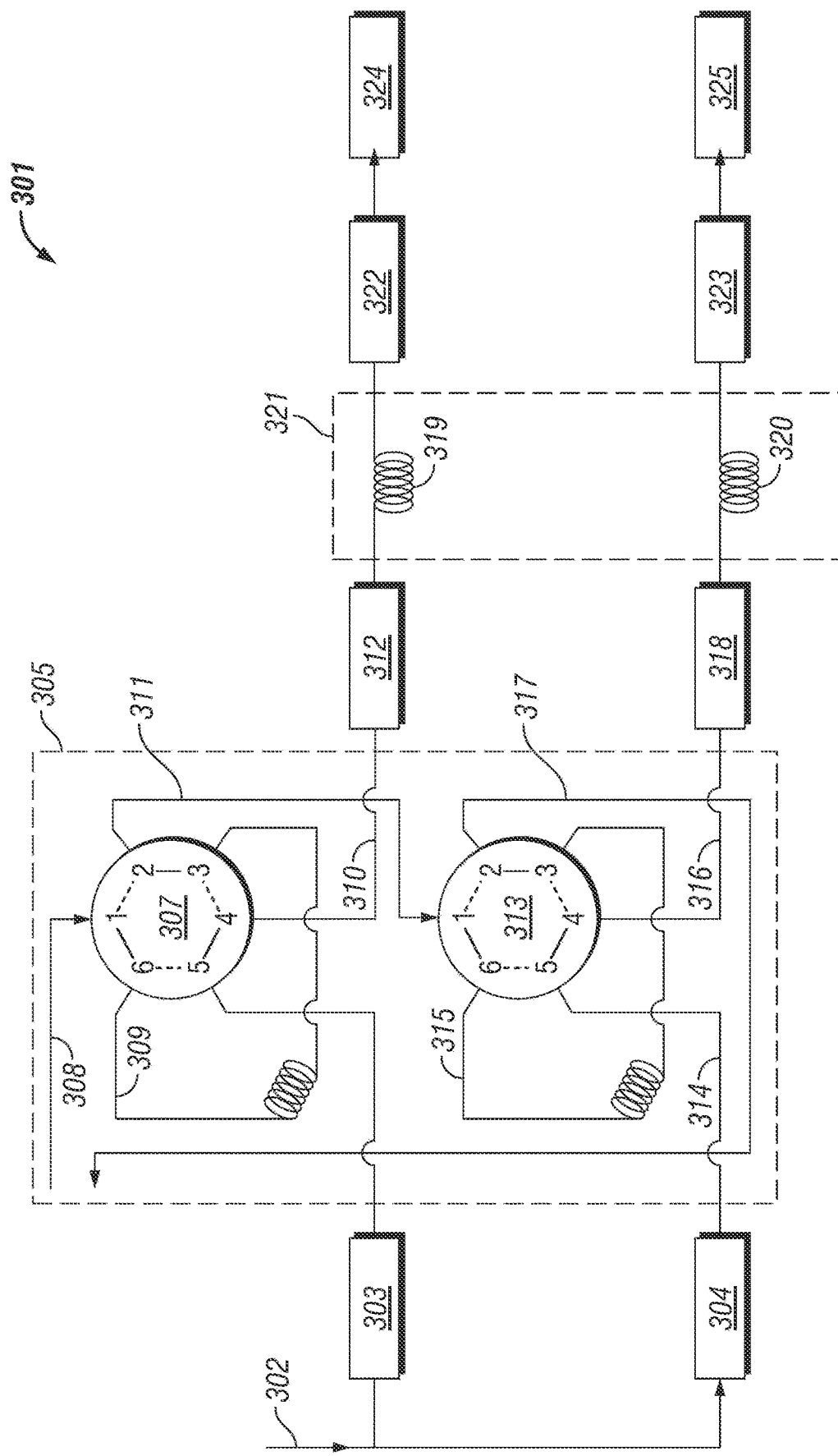

FIG. 3 is a schematic view of a gas chromatography (GC) apparatus (301) for use according to an embodiment of the present disclosure. GC apparatus (301) comprises a feed line (302) for supplying carrier gas (e.g., helium) to a first (303) and a second (304) forward pressure controller. The first forward pressure controller (303) for the carrier gas is fluidly connected through line (306) to a first 6-port switching valve (307) of gas sampling valve system (305). First 6-port switching valve (307) of gas sampling valve system (305) receives process samples or calibration standard samples from an external stream selection system (401) via line (308). First 6-port switching valve (307) is fluidly connected to external sample loop (309), and is fluidly connected through line (310) to a first injector (312) and through line (311) to a second 6-port switching valve (313). Second 6-port switching valve (313) is equipped to receive carrier gas through line (314) via second forward pressure controller (304). Second 6-port switching valve (313) is furthermore fluidly connected to external sample loop (315), through line (316) to a second injector (318), and through line (317) to stream selection system (401). First injector (312) feeds a first chromatographic column (319) which is in fluid communication with a first detector (322). Second injector (318) feeds a second chromatographic column (320) which is in fluid communication with a second detector (323). Chromatographic columns (319) and (320) are held in a temperature-programmed convective oven (321). Injectors (312) and (318) are heated separately at constant measured temperature. Vent flow from first detector (322), typically an FID, goes to atmosphere (324) and vent flow from second detector (323), typically an ECD, goes to low pressure vent header (325). Typically, the column injectors of the GC apparatus are split/splitless injectors. The skilled person will be familiar with the general operation of the GC apparatus and peripheral equipment, including computer software.

When the analyzer is in calibration mode, typically operating software will access a parameter table that contains the composition of each of the components in the halide standard, the nominal calibration gas composition to be produced, the diluent flow required, and the expected flow restrictor exit pressure (nominally 1.6 bara). Furthermore, a wait time for steady state to be reached will be pre-set, as well as a set point for the flow rate of calibration gas (i.e., diluted standard gas) to a stream selection system, a set point for the flow rate of halide standard through the low-flow pressure stabilization flow meter. The current oven temperature will be acquired, the required halide standard flow is determined, and using the Poiseuille equation the halide standard feed pressure controller set point is calculated. When adequate steady-state conditions are reached, the actual restrictor inlet and exit pressures are measured, as well as the actual diluent flow and current oven temperature, and using the Poiseuille equation the actual halide standard flow and the actual calibration gas composition for all components is calculated.

FIG. 4 is a schematic view of a stream selection system (401) suitable for use according to an embodiment of the present disclosure. Stream selection system (401) comprises conduits (402-410) for receiving a plurality of process sample streams. In addition to the process sample streams the stream selector system receives a nitrogen stream (411) for rapid purging of the gas sample loops, a quality control (QC) sample stream (412) for QC purposes and a calibration gas stream (413) from the calibration gas preparation system. The latter three streams are isolated from the main selector valve block (414) by electronically activated single block valves (415), (416), and (417) and (418), respectively. Main selector valve block (414) comprises a plurality of (here 12) dual 3-way valve sets which permit exclusive selection of one of streams (402-410), (412) and (413) for analysis and guarantee that none of the other streams leak into the selected stream. Lines (419) and (420) are for providing gas samples to and from the gas sample valves of GC system (301).

The stream selection system further comprises a plurality of check valves (only 421 marked) for preventing backflow from low pressure vent header (422). The stream selection system is further equipped with gas sampling valve backpressure controller (423) fluidly connected, via a 3-way switching valve, to low pressure vent header (422) and atmospheric vent header (424).

Preferably, the process sample streams, the lines supplying halide standard and diluent to prepare the calibration gas samples, and the gas sampling valves of the analytical apparatus, such as the GC apparatus, are maintained at the same temperature. Accordingly, in one embodiment, the gas blending system, such as gas blending system (101), the gas sampling valves, such as those of sampling valve system (305) of GC apparatus (301), and any means used for directing samples of the gaseous process stream and of the calibration standard gas blend to an analytical apparatus, such as stream selection system (401) are maintained at the same temperature, for instance by containing them in a single oven (102). In one embodiment, the oven that houses the aforementioned components is a convective oven capable of controlling temperature in the range of 50-100° C. The normal set point temperature will be in the range of 60-80° C., preferably about 70° C. The process sample lines that enter the oven need to have enough length inside the oven that the process samples are at the oven temperature when entering the sample loops. The lines supplying halide standard and diluent gas to make the calibration gas samples need to be long enough that the these supplies are at oven temperature in the calibration gas preparation section and in the sample loops. Tubing connecting components in the GC oven and the Stream Selector oven will typically be routed through heated conduit.

In a preferred embodiment, the analyzer for quantitatively analyzing the composition of a gaseous process stream as disclosed herein is an on-line analyzer, or configured to be used as an on-line analyzer, implying that the analyzer is fluidly connected to the process that produces said gaseous process stream, and is capable of conducting continuous automated sampling and quantitative analysis of the process stream while the process is running.

In accordance with another aspect, the present disclosure provides a method for quantitatively analyzing a gaseous process stream comprising one or more gaseous organic halides, said method comprising the steps of (i) withdrawing a sample of a gaseous process stream from one or more sample points in a chemical conversion process;

(ii) supplying the sample of a gaseous process stream to an analyzer as disclosed herein;

(iii) determining the concentration of the gaseous organic halides in the gaseous process stream.

Suitably, prior to step (iii) the one or more detectors of the analytical apparatus of the analyzer have been calibrated for the gaseous organic halides to be analyzed.

In one embodiment, the gaseous process stream comprises one or more gaseous organic halides selected from methyl iodide, ethyl iodide, vinyl iodide, methyl chloride, ethyl chloride, and vinyl chloride. In one embodiment, the gaseous process stream contains at least vinyl iodide, preferably at least methyl iodide, ethyl iodide, and vinyl iodide.

Thus, in one embodiment, the detector of the analytical apparatus has been calibrated for one or more iodides selected from methyl iodide, ethyl iodide and vinyl iodide.

In one embodiment, additionally a detector of the analytical apparatus has been calibrated for one or more chlorides selected from methyl chloride, ethyl chloride, and vinyl chloride.

As disclosed herein before, in one embodiment the analytical apparatus is a gas chromatography (GC) apparatus equipped with Micro Electron Capture Detector (µECD) and a Flame Ionization Detector (FID), wherein iodides in the gaseous process stream are detected by the µECD and chlorides and/or other halides except iodides are detected by the FID, and wherein a linear response of the FID with respect to chloride concentrations is used to verify the accuracy of the calibration of the µECD for low-concentration iodides. In one embodiment, the calibration standards used for calibrating the one or more detectors of the analytical apparatus comprise one or more organic chlorides and one or more organic iodides, wherein the molar ratio of organic chlorides to organic iodides is at least 100:1, preferably at least 500:1 more preferably about 1000:1. Preferably, the molar ratio of organic chlorides to organic iodides is at most 20,000:1, more preferably at most 10,000:1, and most preferably at most 5,000:1.

In a preferred embodiment, the gaseous process stream is withdrawn from a process for the conversion of ethylene to ethylene carbonate and/or ethylene glycol. Typically, the process for the conversion of ethylene to ethylene carbonate and/or ethylene glycol comprises contacting at least a portion of a recycle gas stream comprising one or more iodide impurities with one or more guard bed materials in a guard bed vessel to yield a treated recycle gas stream; and contacting an epoxidation feed gas comprising ethylene, oxygen and at least a portion of the treated recycle gas stream with an epoxidation catalyst to yield an epoxidation reaction product comprising ethylene oxide; and contacting at least a portion of the epoxidation reaction product comprising ethylene oxide with a lean absorbent in the presence of an iodide-containing carboxylation catalyst to yield a fat absorbent stream comprising ethylene carbonate and/or ethylene glycol and the recycle gas stream comprising the one or more iodide impurities.

Accordingly, the present disclosure provides a process for the conversion of ethylene to ethylene carbonate and/or ethylene glycol comprising contacting at least a portion of a recycle gas stream comprising one or more iodide impurities with one or more guard bed materials in a guard bed vessel to yield a treated recycle gas stream; and contacting an epoxidation feed gas comprising ethylene, oxygen and at least a portion of the treated recycle gas stream with an epoxidation catalyst to yield an epoxidation reaction product comprising ethylene oxide; and contacting at least a portion of the epoxidation reaction product comprising ethylene oxide with a lean absorbent in the presence of an iodide-containing carboxylation catalyst to yield a fat absorbent stream comprising ethylene carbonate and/or ethylene glycol and the recycle gas stream comprising the one or more iodide impurities, wherein said process further comprises (i) withdrawing a sample of a gaseous process stream from one or more sample points in the process;

(ii) supplying the sample of the gaseous process stream to an analyzer as disclosed herein;

(iii) determining the concentration of the gaseous organic halides in the gaseous process stream.

Suitably, prior to step (iii) the one or more detectors of the analytical apparatus of the analyzer have been calibrated for the gaseous organic halides to be analyzed, preferably as described herein before. Suitably, the analyzer is an on-line analyzer. Preferably, the sampling of the process stream, the feeding of the sample to the analyzer and the determination of gaseous organic halide concentrations in the sample is carried out in an automated and continuous mode.

Typically, the process stream may be a recycle gas stream in a process for the production of ethylene carbonate and/or ethylene glycol. Preferably, the gaseous process stream is withdrawn at one or more points upstream of an ethylene epoxidation reactor and/or downstream of a guard bed system configured to absorb iodide impurities from the gaseous process stream.

Suitably, the stream may be a stream withdrawn at or near the outlet of an ethylene oxide absorber; a stream withdrawn at or near the inlet of a first guard bed vessel downstream of an ethylene oxide absorber; a stream withdrawn at or near the outlet of a first guard bed vessel downstream of an ethylene oxide absorber and/or at or near the outlet of any subsequent guard bed vessel downstream of said first guard bed vessel; a stream withdrawn at or near the inlet of an ethylene epoxidation reactor; or a stream withdrawn at or near the outlet of an ethylene epoxidation reactor; a stream withdrawn from the outlet of a carbon dioxide absorber upstream of an ethylene epoxidation reactor.

In accordance with another aspect, the present disclosure provides a reaction system for the production of ethylene carbonate and/or ethylene glycol comprising:

a recycle gas loop fluidly connected to a source of ethylene and oxygen;

an epoxidation reactor comprising an epoxidation catalyst, an inlet, and an outlet, wherein the inlet of the epoxidation reactor is fluidly connected to the recycle gas loop;

an ethylene oxide absorber comprising an iodide-containing carboxylation catalyst, an inlet, and an outlet, wherein the outlet of the epoxidation reactor is fluidly connected to the inlet of the ethylene oxide absorber, the outlet of the ethylene oxide absorber is fluidly connected to the recycle gas loop, and the ethylene oxide absorber is configured to produce a recycle gas stream comprising one or more organic halide impurities and a fat absorbent stream comprising ethylene carbonate and/or ethylene glycol;

a first and optionally more guard bed systems downstream of said first guard bed system, each guard bed system comprising an inlet, an outlet and one or more guard bed vessels comprising a guard bed material, wherein the inlet of each guard bed system is fluidly connected to the recycle gas loop, and wherein the guard bed material is configured to remove at least a portion of the one or more organic halide impurities from at least a portion of the recycle gas stream to yield a partially treated recycle gas stream, and wherein said reaction system comprises one or more gas sampling points located at one or more of (i) at or near the outlet of the ethylene oxide absorber;
(ii) at or near the inlet of the first guard bed vessel downstream of the ethylene oxide absorber;
(iii) at or near the outlet of the first guard bed vessel downstream of the ethylene oxide absorber;
(iv) at or near the outlet of each optional guard bed vessel downstream of said first guard bed vessel;
(v) at or near the outlet of a carbon dioxide absorber, wherein the carbon dioxide absorber is upstream of the ethylene epoxidation reactor;
(vi) at or near the inlet of the ethylene epoxidation reactor;
(vii) at our near the outlet of the ethylene epoxidation reactor;

wherein said one or more sampling points are fluidly connected to an analyzer as disclosed herein.

If a vapor-liquid separator (e.g., knock-out vessel, flash vessel, etc.) and/or a recycle gas compressor are present downstream of the ethylene oxide absorber, it is preferred that sampling point (i) is located before these components. With respect to the one or more sampling points (iv), these may be located at or near the outlet of one or more optional additional guard bed vessels located downstream of a first guard bed vessel. Herein, said guard bed vessels may form part of one single guard bed system, or reside in different guard bed systems, for example different guard bed systems for specifically absorbing different (halide) impurities.

Each guard bed system preferably comprises two or more guard bed vessels, each guard bed vessel comprising an inlet, an outlet and a packed bed of guard bed material. Optionally, each guard bed system comprises more than two, for example three or four, guard bed vessels. The number of guard bed vessels contained within each guard bed system may be the same or different. Within a given guard bed system, the guard bed vessels may be arranged in parallel with associated switching means to allow the process to be switched between the vessels, thus maintaining a continuous operation of the process. Alternatively, the guard bed vessels within a guard bed system may be arranged in series or in series in sequential order, with associated valves, as described in co-pending application EP15200254.9.

A particular advantage of the present disclosure is that it allows guard bed vessels inserted in a process gas stream for removing iodide impurities to be operated such that a very high proportion of said impurities present in the recycle gas stream are removed, since it allows recurrent, on-line monitoring of iodide levels at any desired position of the process, and (thus) to rapidly identify trends in and make predictions of halide production and guard bed capacity utilization. Consequently, it allows minimizing operating expenses of guard bed systems by maximizing the utilization thereof.

Figure 5:
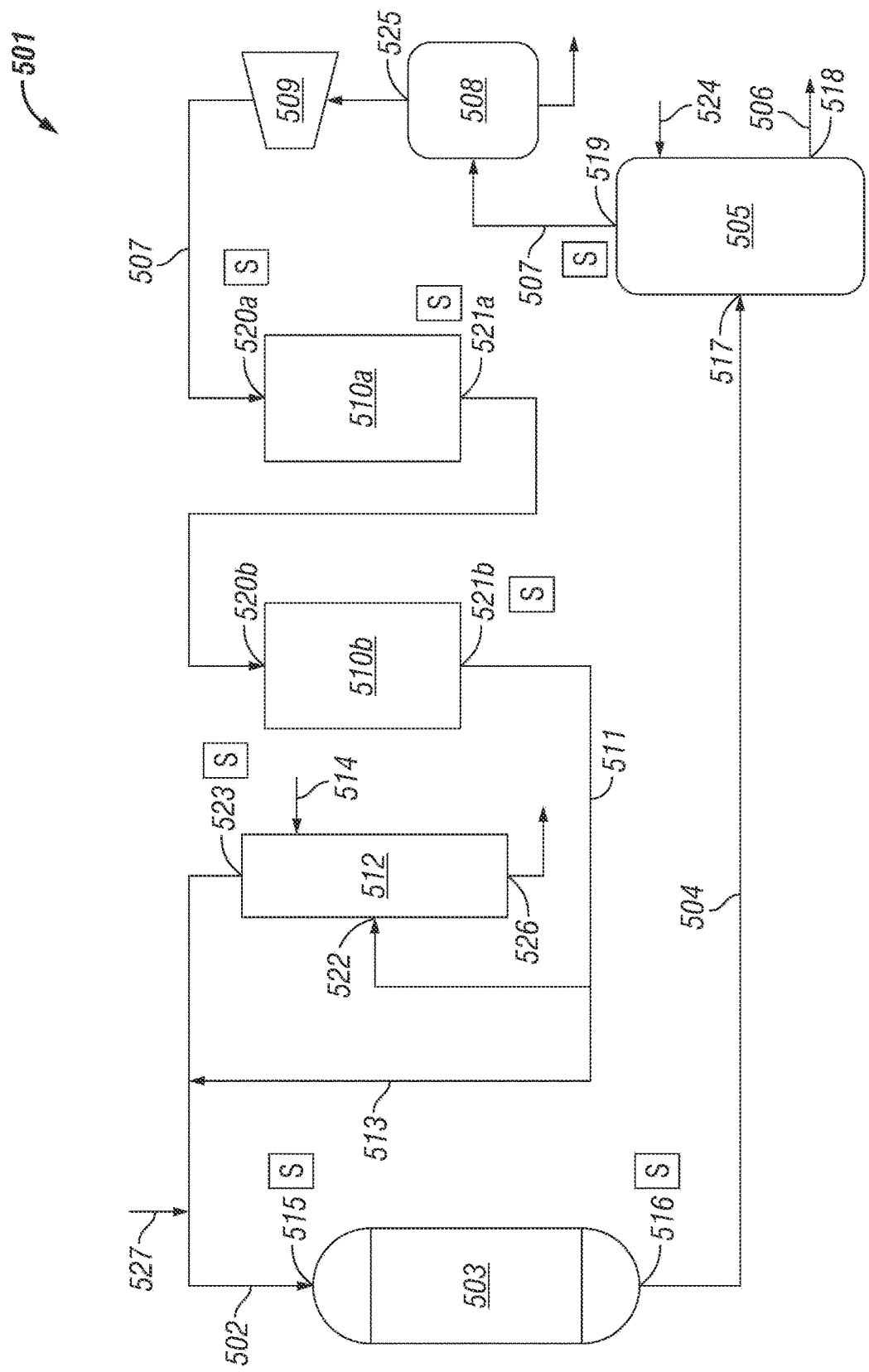

FIG. 5 is a schematic view of a reaction system (501) for the production of ethylene carbonate and/or ethylene glycol, according to an embodiment of the present disclosure. Reaction system (501) generally comprises ethylene epoxidation reactor (503), ethylene oxide absorber (505), at least one guard bed system (510) comprising at least one guard bed vessel (510a), and optionally a second guard bed vessel (510b), and third, fourth, etc. guard bed vessels (not shown), and carbon dioxide absorber (512). As shown in FIG. 5, epoxidation feed gas (502) is supplied to ethylene epoxidation reactor (503) via an inlet, such as inlet (515), which is in fluid communication with the recycle gas loop. Components of epoxidation feed gas (502) include at least a portion of guard bed-treated recycle gas stream (511) and typically further comprise ethylene, oxygen, ballast gas (e.g., methane or nitrogen), and a reaction modifier (e.g., monochloroethane, vinyl chloride or dichloroethane), which may be supplied to the recycle gas loop via one or more inlets, such as inlet (527). In ethylene epoxidation reactor (503), ethylene is reacted with oxygen in the presence of an epoxidation catalyst to yield epoxidation reaction product stream (504), which typically comprises ethylene oxide, unreacted ethylene and oxygen, reaction modifier, ballast gas, various by-products of the epoxidation reaction (e.g., carbon dioxide and water) and various impurities. Epoxidation reaction product stream (504) exits ethylene epoxidation reactor (503) via an outlet, such as outlet (516), which is in fluid communication with an inlet of ethylene oxide absorber (505), such as inlet (517). Preferably, epoxidation reaction product stream (504) is cooled in one or more coolers (not shown), preferably with generation of steam at one or more temperature levels before being supplied to ethylene oxide absorber (505). Epoxidation reaction product stream (504) and lean absorbent stream (524) are supplied to ethylene oxide absorber (505). In ethylene oxide absorber (505), the epoxidation reaction product is brought into intimate contact with the lean absorbent in the presence of an iodide-containing carboxylation catalyst, and more preferably in the presence of an iodide-containing carboxylation catalyst and a hydrolysis catalyst. At least a portion of, and preferably substantially all of, the ethylene oxide in the epoxidation reaction product is absorbed into the lean absorbent. Fat absorbent stream (506), which comprises ethylene carbonate and/or ethylene glycol, is withdrawn from ethylene oxide absorber (505) via an outlet, such as outlet (518) and may optionally be supplied to one or more finishing reactors (not shown). Any gases not absorbed in ethylene oxide absorber (505) are withdrawn at or near the top of ethylene oxide absorber (505) as recycle gas stream (507) via an outlet, such as outlet (519), which is in fluid communication with the recycle gas loop. The recycle gas loop comprises interconnecting pipework between outlet (519) of ethylene oxide absorber (505) and inlet (515) of ethylene epoxidation reactor (503) and optionally may further comprise heat exchanger(s), a vapor-liquid separator, such as vapor-liquid separator (508) (e.g., knock-out vessel, flash vessel, etc.), a recycle gas compressor, such as recycle gas compressor (509), and/or a carbon dioxide absorber, such as carbon dioxide absorber (512). Recycle gas stream (507) may comprise a vinyl iodide impurity due to the presence of the iodide-containing carboxylation catalyst in ethylene oxide absorber (505) and the reaction conditions therein. The recycle gas stream may further comprise an alkyl iodide impurity, such as methyl iodide, ethyl iodide, or a combination thereof. Typically, recycle gas stream (507) further comprises one or more of ethylene, oxygen, reaction modifier, ballast gas, carbon dioxide and water. To reduce the amount of the vinyl iodide and/or alkyl iodide impurities, recycle gas stream (507) is supplied to one or more guard bed systems (510), with a first guard bed vessel (510a) and optionally second (510b), third, fourth etc. (not shown) guard bed vessels, via an inlet, such as inlet (520), with first inlet (520a) and optionally second (520b), third, fourth etc. (not shown) inlets, that are in fluid communication with the recycle gas loop.

In the one or more guard bed systems (510) comprising one or more guard bed vessels, recycle gas stream (507) is brought into contact with a packed bed of guard bed material in a guard bed vessel. By contacting recycle gas stream (507) with the guard bed material, at least a portion of the vinyl iodide and/or alkyl iodide impurities are removed from recycle gas stream (507) to yield treated recycle gas stream (511), which comprises a reduced amount of the vinyl iodide and/or alkyl iodide impurities relative to recycle gas stream (507). Treated recycle gas stream (511) exits the one or more guard bed systems (510) via an outlet, such as outlet (521), which is in fluid communication with the recycle gas loop. Suitably, the one or more guard bed systems (510) may be located anywhere in the recycle gas loop. For example, as shown in FIG. 5, the one or more guard bed systems (510) may preferably be located in the recycle gas loop between outlet (519) of ethylene oxide absorber (505) and an inlet of carbon dioxide absorber (512), such as inlet (522), and more preferably between an outlet of recycle gas compressor (509) and inlet (522) of carbon dioxide absorber (512). Also, as shown in FIG. 5, one or more guard bed systems (510) comprising one or more guard bed vessels may preferably be located in the recycle gas loop between an outlet of vapor-liquid separator (508), such as outlet (525), and inlet (515) of ethylene epoxidation reactor (503), and more preferably between outlet (525) of vapor-liquid separator (508) and inlet (522) of carbon dioxide absorber (512). Further, as shown in FIG. 5, one or more guard bed systems (510) may preferably be located in the recycle gas loop upstream from inlet (527), where additional component(s) of epoxidation feed gas (502), such as ethylene, oxygen, ballast gas and/or a reaction modifier, may be supplied to the recycle gas loop. Preferably, as shown in FIG. 5, at least a portion of treated recycle gas stream (511) is supplied to carbon dioxide absorber (512) via an inlet, such as inlet (522), along with recirculating absorbent stream (514). In carbon dioxide absorber (512), the treated recycle gas stream is brought into contact with recirculating absorbent stream (514). At least a portion of the carbon dioxide in the treated recycle gas stream is absorbed into the recirculating absorbent stream and is withdrawn from carbon dioxide absorber (512) via an outlet, such as outlet (526). The portion of the treated recycle gas stream that was supplied to carbon dioxide absorber (512), but that was not absorbed by the recirculating absorbent stream exits via an outlet, such as outlet (523), and is preferably re-combined with any portion of the treated recycle gas stream that bypassed carbon dioxide absorber (512) via bypass (513). The treated recycle gas stream is then recycled to inlet (515) of ethylene epoxidation reactor (503) as a component of epoxidation feed gas (502). In accordance with the present disclosure, reaction system (501) comprises one or more sampling points (S) for withdrawing one or more samples of the gas streams present in reaction system (501) for on-line quantitative analysis of vinyl iodide and/or alkyl iodide impurities. Said one or more sampling points (S) may be located at or near outlet (519) of ethylene oxide absorber (505), preferably before vapor-liquid separator (508) and recycle compressor recycle gas compressor (509); at or near inlet (520a) of first guard bed vessel (510a); at or near outlet (521a) of first guard bed vessel (510a); at or near outlet (521b) of second guard bed vessel (510b); at or near the outlet of any third, second, etc. guard bed vessel; at or near outlet (523) of carbon dioxide absorber (512); at or near inlet (515) of ethylene epoxidation reactor (503); at or near outlet (516) of ethylene epoxidation reactor (503); and any combination of the foregoing sampling points. Preferably, sampling points (S) are present in all of the aforementioned locations in reaction system (501) and indicated in FIG. 5.

EXAMPLES

Table 1 displays the sequence of operating steps performed on the gas blending system to prepare a diluted calibration standard with desired nominal concentration (with 50 ppbv ethyl iodide as target concentration) from a halide standard gas with known concentrations of methyl iodide (MI), ethyl iodide (EI), vinyl iodide (VI), methyl chloride (MC), ethyl chloride (EC), and vinyl chloride (VC), using nitrogen as diluent gas.

TABLE 1

Sequence of Operation for Making Calibration Gas Sample

| Step | Parameter |
|---|---|
| 1) Access Data Table | |
| Halide std. compositions (VC, EC, MC, VI, EI, MI) | 2100 ppmv, 2050 ppmv, 1980 ppmv, 2050 ppbv, 2100 ppbv (master component), 2150 ppbv |
| Nominal calibr. gas composition | 50 ppbv ethyl iodide |
| Diluent flow ($Q_{dil}$) [sccm] [107 in FIG. 1] | 1000 |
| Wait time—min | 3 |
| Halide std. press stabilization flow [sccm] [122 in FIG. 1] | 0 |
| Calibration gas flow to Stream Sel. [sccm] [149 in FIG. 1] | 50 |
| Expected capillary exit pressure ($P_2$) [bara] [151 in FIG. 1] | 1.6 |
| Poiseuille flow para. ($C_o$) [Km$^5$/N] | 5.854E−20 |
| 2) Acquire Data | |
| Current oven temperature [° C.] | 70 (343.15 K) |
| 3) Calculate | |
| Gas viscosity ($\mu$) at oven temp [Ns/m$^2$] | 1.978E−05 |
| Halide std. flow required (Q) [sccm] | $= \dfrac{Q_{dil} \cdot ppbv_{cal\,gas}}{ppbv_{std} - ppbv_{cal\,gas}} = \dfrac{1000 \cdot 50}{2100 - 50} = 24.39$ sccm $= 4.065\text{E}{-}7$ m3/s |
| Capillary inlet pressure ($P_1$) [bara] | $= \sqrt{P_2^2 + \dfrac{QT_{oven}\mu}{C_o}} = 7.049$ bara |
| 4) Input set points and wait 3 minutes | |
| Halide supply pressure ($P_1$) [113 in FIG. 1] | 7.049 bara |
| Halide Std. pressure stabilization flow [122 in FIG. 1] | 0 sccm |
| Cal. Gas. back pressure regulator [151 in FIG. 1] | 1.6 bara |
| Cal. Gas Flow to stream selector [149 in FIG. 1] | 50 sccm |
| 5) Acquire Data | |
| Halide Supply pressure capillary inlet Pressure ($P_1$) [bara] [113 in FIG. 1] | 7.062 |
| Capillary exit pressure ($P_2$) [bara] [144 in FIG. 1] | 1.622 |
| Oven temperature | 70.1° C. (343.25 K) |
| Diluent flow [107 in FIG. 1] | 1001 sccm |
| 6) Calculate | |
| Gas viscosity ($\mu$) at oven temp [Ns/m$^2$] | 1.980E−05 |
| Halide standard flow | $Q = \dfrac{C_o}{T_{oven}\mu}(P_1^2 - P_2^2) = 25.04$ sccm |
| Actual calibration standard concentrations | $= \dfrac{Q}{Q + Q_{dil}}\,ppm(b)v_{std}$ |
| VC | 51.3 ppmv |
| EC | 50.0 ppmv |
| MC | 48.3 ppmv |
| VI | 50.0 ppbv |
| EI | 51.3 ppbv |
| MI | 52.5 ppbv |

The operational sequence given in Table 1 is used to generate a series of calibration gases which are used to provide a full-range calibration of a GC apparatus. Table 2 sets the nominal flow rates of the halide standard and diluent gas needed to produce the calibration gas compositions. Table 2 also provides capillary inlet and outlet pressures that will produce the required halide standard flow.

Figure 6:
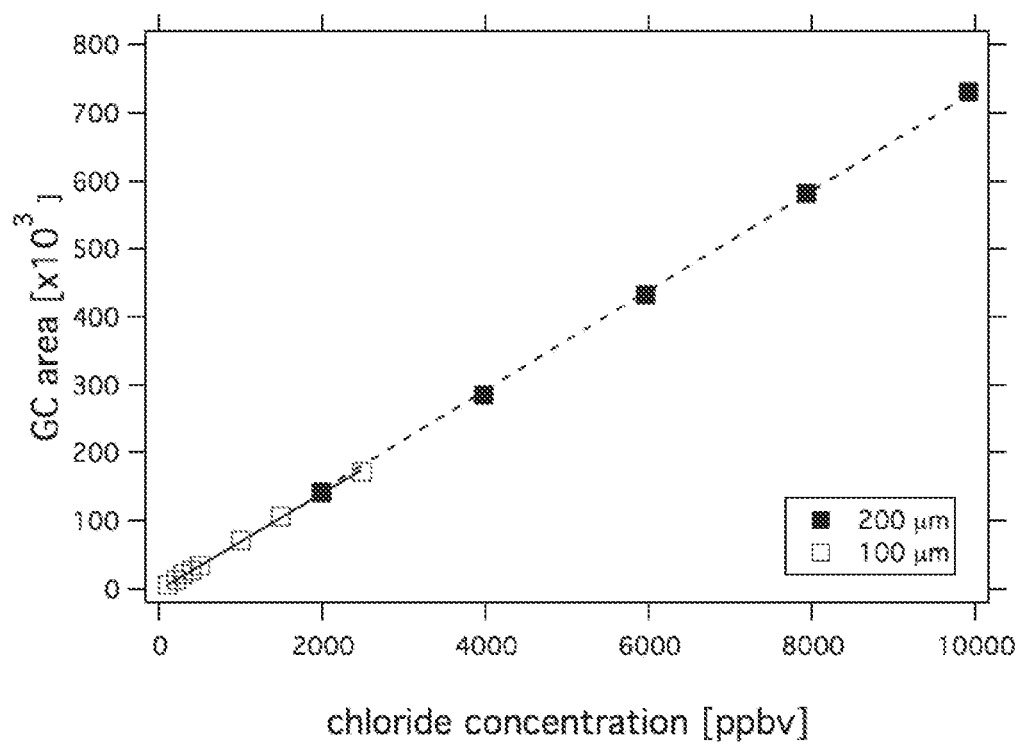
FIG. 6 shows an FID detector output as a function of methyl chloride concentration.

FIG. 6. shows the response of an FID detector in a GC apparatus to a series of samples with different methyl chloride (MC) concentrations. The open squares represent the detector output for samples obtained with a gas blending (dilution) system using a capillary flow restrictor with 100 μm nominal internal diameter (10 m length); the closed squares represent samples obtained using a capillary flow restrictor with 200 μm nominal internal diameter (30 m length). The dashed line and solid line are linear fits to the data using identical fit parameters. These data show that using as gas blending system with flow restrictors as herein defined, broad, overlapping concentration ranges for calibration standards can be obtained. The data further demonstrate the fully linear dependence of FID detector response to analyte concentration.

Figure 7:
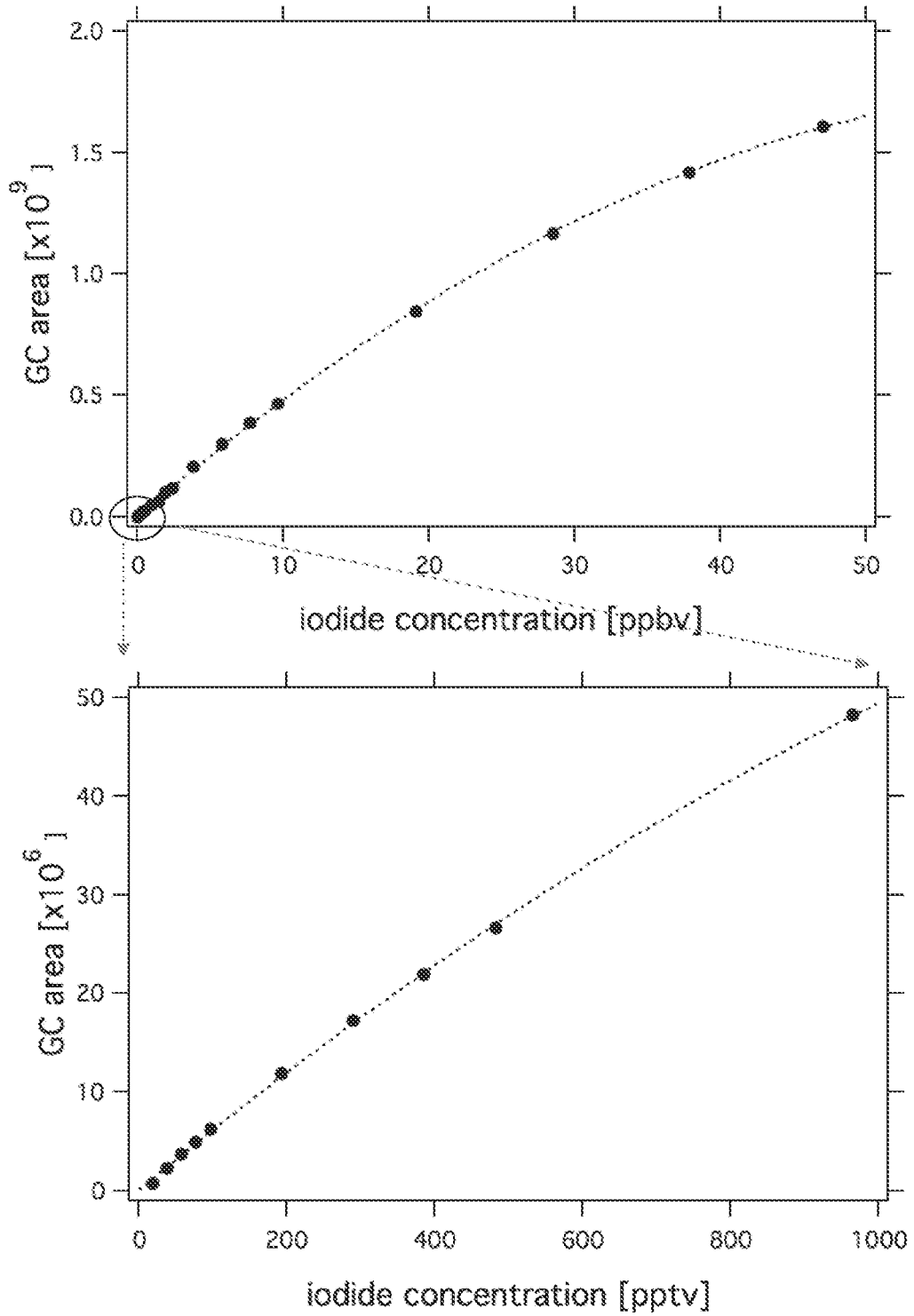
FIG. 7 shows a µECD detector output as a function of ethyl iodide concentration.

FIG. 7. shows the response of a μECD detector as a function of ethyl iodide (EI) concentration. The top graph shows the detector output for the full range of diluted samples, said samples being obtained by dilution with inert ($N_2$) gas using a capillary flow restrictor with 100 μm nominal internal diameter (10 m length) and a capillary flow restrictor with 200 μm nominal internal diameter (30 m length). The bottom graph displays the same data, but only showing the <1000 pptv concentration range. The dotted line is a power law fit (with exponent ~0.8) to the data.

Figure 8:
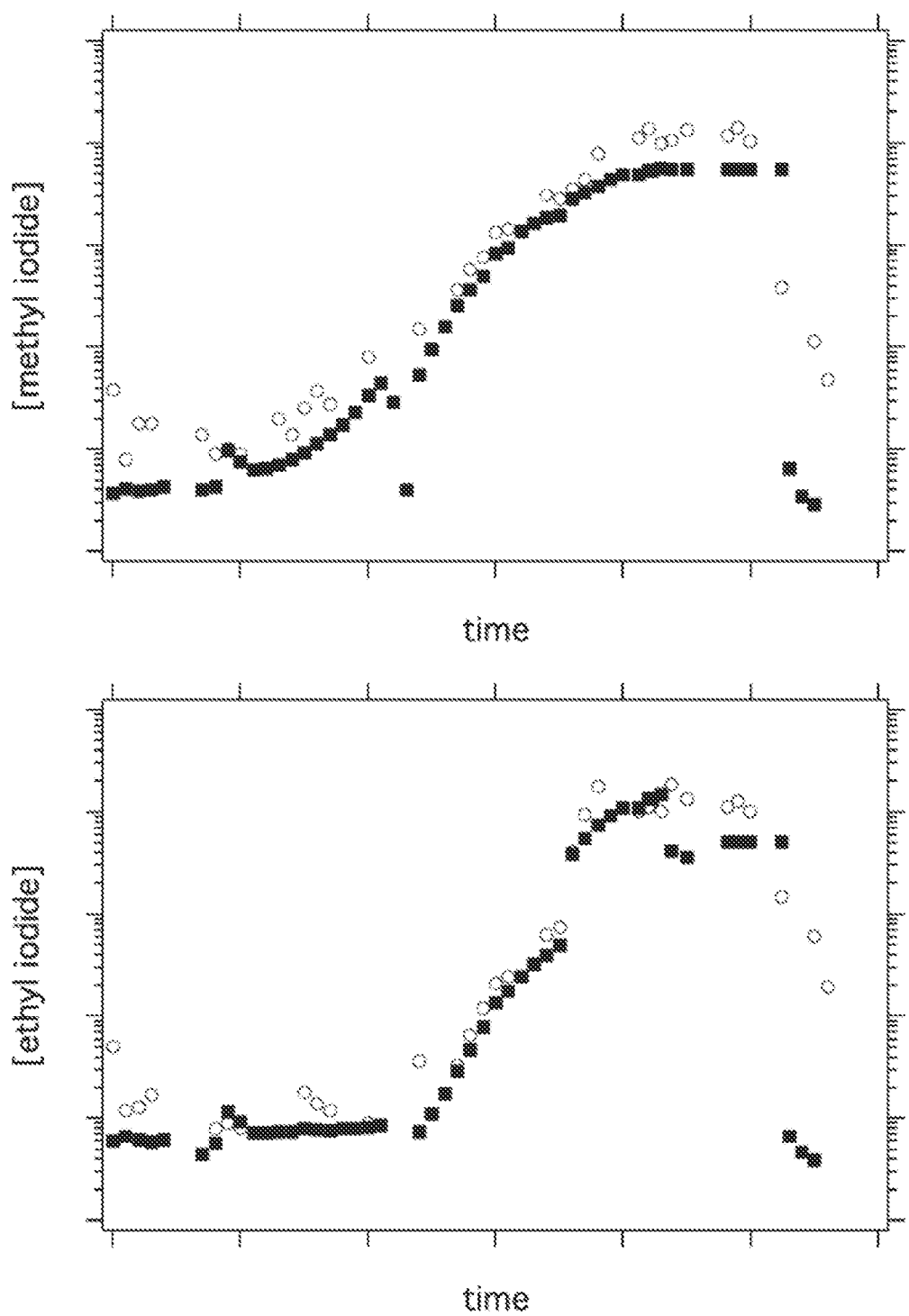
FIG. 8 shows a comparison of on-line and off-line analysis of methyl iodide and ethyl iodide in a recycle gas stream of a process for the production of ethylene carbonate and/or ethylene glycol.

FIG. 8. shows methyl iodide (top) and ethyl iodide (bottom) concentrations as a function of time as measured at the outlet of a guard bed vessel (first guard bed vessel in a guard bed system comprising four guard bed vessels) in a process for the production of ethylene carbonate and/or ethylene glycol, using an on-line analyzer (closed squares) as disclosed herein and using off-line analysis by GC-MS (open circles). Note the logarithmic vertical axis.

TABLE 2

Halide Standard and Required Diluent Flows and Capillary Pressures

| | MC ppm | EC ppm | VC ppm | MI ppb | EI ppb | VI ppb | Standard Gas Flow through Capillary sccm | Dil. Flow sccm | $P_1$ Stabil. Flow [through 122] sccm | $P_1$ bara | $P_2$ bara |
|---|---|---|---|---|---|---|---|---|---|---|---|
| Standard gas | 2000 | 2000 | 2000 | 2000 | 2000 | 2000 | | | | | |
| High Range Calibration Gas | | | | | | | | | | | |
| | 500 | 500 | 500 | 500 | 500 | 500 | 41.67 | 125 | 0 | 9.115 | 1.60 |
| | 200 | 200 | 200 | 200 | 200 | 200 | 27.78 | 250 | 0 | 7.500 | 1.60 |
| | 100 | 100 | 100 | 100 | 100 | 100 | 26.32 | 500 | 0 | 7.309 | 1.60 |
| | 50 | 50 | 50 | 50 | 50 | 50 | 25.64 | 1000 | 0 | 7.219 | 1.60 |
| | 20 | 20 | 20 | 20 | 20 | 20 | 10.10 | 1000 | 0 | 4.632 | 1.60 |
| | 10 | 10 | 10 | 10 | 10 | 10 | 5.030 | 1000 | 0 | 3.503 | 1.60 |
| | 5 | 5 | 5 | 5 | 5 | 5 | 2.506 | 1000 | 2 | 2.721 | 1.60 |
| Low Range Calibration Gas | | | | | | | | | | | |
| | 2 | 2 | 2 | 2 | 2 | 2 | 1.001 | 1000 | 3 | 5.789 | 1.60 |
| | 1 | 1 | 1 | 1 | 1 | 1 | 0.500 | 1000 | 3 | 4.246 | 1.60 |
| | 0.5 | 0.5 | 0.5 | 0.5 | 0.5 | 0.5 | 0.250 | 1000 | 3 | 3.208 | 1.60 |
| | 0.2 | 0.2 | 0.2 | 0.2 | 0.2 | 0.2 | 0.100 | 1000 | 3 | 2.242 | 1.60 |
| | 0.1 | 0.1 | 0.1 | 0.1 | 0.1 | 0.1 | 0.050 | 1000 | 3 | 2.026 | 1.60 |
| | 0.05 | 0.05 | 0.05 | 0.05 | 0.05 | 0.05 | 0.025 | 1000 | 3 | 1.826 | 1.60 |
| | 0.02 | 0.02 | 0.02 | 0.02 | 0.02 | 0.02 | 0.010 | 1000 | 3 | 1.694 | 1.60 |

We claim:

1. A method for calibrating a detector in an analytical apparatus for quantitatively analyzing one or more components in a gaseous stream, comprising the steps of
   (i) providing a standard gas, wherein said standard gas contains each of the components to be analyzed in a fixed concentration, and an inert diluent gas;
   (ii) feeding the standard gas and the diluent gas to a gas blending system to obtain a diluted standard gas sample having a known concentration;
   feeding the diluted standard gas sample obtained in step (ii) to the analytical apparatus and recording a detector output for said sample;
   (iv) repeating steps (ii) and (iii) at least twice in succession to obtain a series of diluted standard gas samples having different concentrations and corresponding detector outputs;
   (v) combining the corresponding detector outputs for the diluted standard gas samples to generate a calibration curve for the detector,
   wherein said gas blending system comprises
   (a) a first mass flow controller or a forward pressure controller for separately controlling the flow rate or pressure, respectively, of the standard gas supplied to each of two or more different flow restrictor devices arranged in parallel, wherein the two or more flow restrictor devices each have a restrictor inlet for receiving and each have a restrictor outlet for discharging the standard gas, wherein said restrictor outlet is fluidly connected to the forward pressure controller for measuring the pressure of the standard gas stream discharged from the flow restrictor device, and wherein dimensions of the two or more flow restrictor devices are selected such that each flow restrictor device produces a different controlled volumetric flow rate of the standard gas at the restrictor outlet, and (b) a second mass flow controller for controlling the flow rate of a diluent gas supplied to a multi-port flow selector device, wherein said multi-port flow selector device comprises a selector inlet for receiving and at least two selector outlets for removing the diluent gas at a controlled volumetric flow rate, (c) at least two or more mixing zones, each mixing zone located downstream of a respective flow restrictor device of the two or more flow restrictor devices and the multi-port flow selector device, wherein each mixing zone comprises a first mixing inlet for receiving standard gas from the restrictor outlet of the flow restrictor device fluidly connected to it, a second mixing inlet for receiving diluent gas from one of the at least two selector outlets of the multi-port flow selector device and a mixing outlet for discharging a diluted standard gas sample, and wherein said series of diluted standard gas samples having different concentrations is obtained by using the multi-port flow selector device to selectively direct flow of the diluent gas to each of the mixing zones, and by successively adjusting the volumetric flow rate of the standard gas from the restrictor outlet of the flow restrictor device supplied to each mixing zone, and optionally adjusting the volumetric flow rate of the diluent gas supplied to each of the mixing zones, to produce a variety of mixing ratios of standard gas and diluent gas.

2. The method according to claim 1, wherein the analytical apparatus comprises a first detector with non-linear response to analyte concentration and a second detector with linear response to analyte concentration, wherein the analyte concentrations detected by the first detector are lower than the analyte concentrations detected by the second detector and wherein a linear response of the second detector is used to validate the accuracy of the calibration of the first detector.

* * * * *

UNITED STATES PATENT AND TRADEMARK OFFICE
CERTIFICATE OF CORRECTION

| | |
|---|---|
| PATENT NO. | : 11,774,420 B2 |
| APPLICATION NO. | : 17/852005 |
| DATED | : October 3, 2023 |
| INVENTOR(S) | : Jesse Raymond Black et al. |

It is certified that error appears in the above-identified patent and that said Letters Patent is hereby corrected as shown below:

In the Specification

In Column 5, Line 43, delete "gas system" and insert -- gas blending system --.

In Column 5, Line 54, delete "pas" and insert -- gas --.

In Column 6, Line 19, delete "pas" and insert -- gas --.

In Column 6, Line 36, delete "rate (c)" and insert -- rate, (c) --.

In Column 6, Line 41, delete "to it" and insert -- to it, --.

In Column 17, Line 41, delete "ii)" and insert -- (ii) --.

In the Claims

In Column 30, Line 42, in Claim 1, delete "feeding" and insert -- (iii) feeding --.

In Column 30, Line 54, in Claim 1, delete "the flow" and insert -- flow --.

Signed and Sealed this
Thirtieth Day of January, 2024

Katherine Kelly Vidal
*Director of the United States Patent and Trademark Office*